(12) United States Patent
Blain et al.

(10) Patent No.: US 11,272,961 B2
(45) Date of Patent: Mar. 15, 2022

(54) APPARATUS FOR BONE STABILIZATION AND DISTRACTION AND METHODS OF USE

(71) Applicant: Spinal Elements, Inc., Carlsbad, CA (US)

(72) Inventors: Jason Blain, Encinitas, CA (US); Gregory Martin, Carlsbad, CA (US)

(73) Assignee: Spinal Elements, Inc., Carlsbad, CA (US)

(*) Notice: Subject to any disclaimer, the term of this patent is extended or adjusted under 35 U.S.C. 154(b) by 17 days.

(21) Appl. No.: 16/287,206

(22) Filed: Feb. 27, 2019

(65) Prior Publication Data

US 2019/0192194 A1 Jun. 27, 2019

Related U.S. Application Data

(60) Continuation of application No. 15/215,137, filed on Jul. 20, 2016, now Pat. No. 10,251,679, which is a
(Continued)

(51) Int. Cl.
*A61B 17/70* (2006.01)
*A61B 17/56* (2006.01)
*A61B 17/68* (2006.01)

(52) U.S. Cl.
CPC ...... *A61B 17/7053* (2013.01); *A61B 17/7035* (2013.01); *A61B 17/7064* (2013.01);
(Continued)

(58) Field of Classification Search
CPC ............ A61B 17/7043; A61B 17/7049; A61B 17/705; A61B 17/7052; A61B 17/7062;
(Continued)

(56) References Cited

U.S. PATENT DOCUMENTS

| | | |
|---|---|---|
| 86,016 A | 1/1869 | Howell |
| 1,630,239 A | 5/1927 | Binkley et al. |

(Continued)

FOREIGN PATENT DOCUMENTS

| | | |
|---|---|---|
| CA | 2 437 575 | 4/2009 |
| DE | 93 04 368 | 5/1993 |

(Continued)

OTHER PUBLICATIONS

3rd Party Lab Notebook, "Facet Cartilage Repair," dated May 20, 2003 in 2 pages.
(Continued)

*Primary Examiner* — Julianna N Harvey
(74) *Attorney, Agent, or Firm* — Knobbe, Martens, Olson & Bear, LLP

(57) ABSTRACT

In some embodiments, a method includes disposing a flexible band through an aperture of a support member, the support member having a fixation portion configured to secure the support member to a first bone portion. The method includes advancing a portion of the flexible band through an attachment portion of the flexible band until the flexible band is secured to a second bone portion. The method includes advancing a portion of the fixation portion of the support member into the first bone portion until the support member is secured to the first bone portion.

15 Claims, 15 Drawing Sheets

Related U.S. Application Data division of application No. 13/804,521, filed on Mar. 14, 2013, now Pat. No. 9,421,044.

(52) U.S. Cl.
CPC .... *A61B 17/7067* (2013.01); *A61B 2017/567* (2013.01); *A61B 2017/681* (2013.01); *A61B 2017/7073* (2013.01)

(58) Field of Classification Search
CPC ............ A61B 17/7053; A61B 17/7067; A61B 17/7068
See application file for complete search history.

(56) References Cited

U.S. PATENT DOCUMENTS

| | | |
|---|---|---|
| 1,822,280 A | 9/1931 | Ervay |
| 1,822,330 A | 9/1931 | Anslie |
| 2,486,303 A | 10/1949 | Longfellow |
| 2,706,023 A | 4/1955 | Merritt |
| 2,967,282 A | 1/1961 | Schwartz et al. |
| 3,111,945 A | 11/1963 | Von Solbrig |
| 3,149,808 A | 9/1964 | Weckesser |
| 3,570,497 A | 3/1971 | Lemole |
| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,164,793 A | 8/1979 | Swanson |
| 4,166,292 A | 9/1979 | Bokros |
| 4,231,121 A | 11/1980 | Lewis |
| D261,935 S | 11/1981 | Halloran |
| 4,312,337 A | 1/1982 | Donohue |
| 4,323,217 A | 4/1982 | Dochterman |
| 4,349,921 A | 9/1982 | Kuntz |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,573,458 A | 3/1986 | Lower |
| 4,573,459 A | 3/1986 | Litton |
| 4,634,445 A | 1/1987 | Helal |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,880,429 A | 11/1989 | Stone |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,959,065 A | 9/1990 | Arnett et al. |
| 4,969,909 A | 11/1990 | Barouk |
| 5,000,165 A | 3/1991 | Watanabe |
| 5,002,546 A | 3/1991 | Romano |
| 5,011,484 A | 4/1991 | Bréard |
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,112,013 A | 5/1992 | Tolbert et al. |
| 5,112,346 A | 5/1992 | Hiltebrandt et al. |
| 5,127,912 A | 7/1992 | Ray et al. |
| 5,135,188 A | 8/1992 | Anderson et al. |
| 5,147,404 A | 9/1992 | Downey |
| 5,171,280 A | 12/1992 | Baumgartner |
| 5,192,326 A | 3/1993 | Bao et al. |
| 5,192,327 A | 3/1993 | Brantigan |
| 5,209,755 A | 5/1993 | Abrahan et al. |
| 5,258,031 A | 11/1993 | Salib et al. |
| 5,282,861 A | 2/1994 | Kaplan |
| 5,286,249 A | 2/1994 | Thibodaux |
| 5,300,073 A | 4/1994 | Ray et al. |
| 5,306,275 A | 4/1994 | Bryan |
| 5,306,308 A | 4/1994 | Gross et al. |
| 5,306,309 A | 4/1994 | Wagner et al. |
| 5,326,364 A | 7/1994 | Clift, Jr. et al. |
| 5,330,479 A | 7/1994 | Whitmore |
| 5,360,431 A | 11/1994 | Puno et al. |
| 5,368,596 A | 11/1994 | Burkhart |
| 5,370,697 A | 12/1994 | Baumgartner |
| 5,372,598 A | 12/1994 | Luhr et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A * | 10/1995 | Alesi, Jr. .............. A61B 17/823 24/16 R |
| 5,487,756 A | 1/1996 | Kallesoe et al. |
| 5,491,882 A | 2/1996 | Walston et al. |
| 5,496,142 A | 3/1996 | Fodor et al. |
| 5,496,318 A | 3/1996 | Howland et al. |
| 5,507,823 A | 4/1996 | Walston et al. |
| 5,509,918 A | 4/1996 | Romano |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,105 A | 11/1996 | Gundolf |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,713,542 A | 2/1998 | Benoit |
| 5,716,415 A | 2/1998 | Steffee |
| 5,725,582 A | 3/1998 | Bevan et al. |
| 5,741,260 A | 4/1998 | Songer et al. |
| 5,741,261 A | 4/1998 | Moskovitz et al. |
| D395,138 S | 6/1998 | Ohata |
| 5,766,251 A | 6/1998 | Koshino |
| 5,766,253 A | 6/1998 | Brosnahan |
| 5,772,663 A | 6/1998 | Whiteside et al. |

(56) References Cited

U.S. PATENT DOCUMENTS

| | | |
|---|---|---|
| 5,797,916 A | 8/1998 | McDowell |
| 5,824,093 A | 10/1998 | Ray et al. |
| 5,824,094 A | 10/1998 | Serhan et al. |
| 5,836,948 A | 11/1998 | Zucherman et al. |
| 5,851,208 A | 12/1998 | Trott |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,879,396 A | 3/1999 | Walston et al. |
| 5,888,203 A | 3/1999 | Goldberg |
| 5,893,889 A | 4/1999 | Harrington |
| 5,895,428 A | 4/1999 | Berry |
| RE36,221 E | 6/1999 | Rd et al. |
| 5,918,604 A | 7/1999 | Whelan |
| 5,951,555 A | 9/1999 | Rehak et al. |
| 5,964,765 A | 10/1999 | Fenton et al. |
| 5,993,452 A | 11/1999 | Vandewalle |
| 5,997,542 A | 12/1999 | Burke |
| 6,001,130 A | 12/1999 | Bryan et al. |
| 6,014,588 A | 1/2000 | Fitz |
| 6,019,763 A | 2/2000 | Nakamura et al. |
| 6,019,792 A | 2/2000 | Cauthen |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,099,531 A | 8/2000 | Bonutti |
| 6,102,347 A | 8/2000 | Benoit |
| 6,106,558 A | 8/2000 | Picha |
| 6,113,637 A | 9/2000 | Gill et al. |
| 6,132,464 A | 10/2000 | Martin |
| 6,132,465 A | 10/2000 | Ray et al. |
| 6,146,422 A | 11/2000 | Lawson |
| 6,156,067 A | 12/2000 | Bryan et al. |
| 6,179,839 B1 | 1/2001 | Weiss et al. |
| D439,340 S | 3/2001 | Michelson |
| 6,200,322 B1 | 3/2001 | Branch et al. |
| 6,293,949 B1 | 9/2001 | Justis et al. |
| D450,122 S | 11/2001 | Michelson |
| 6,325,803 B1 | 12/2001 | Schumacher et al. |
| D454,953 S | 3/2002 | Michelson |
| 6,368,325 B1 | 4/2002 | McKinley et al. |
| 6,368,350 B1 | 4/2002 | Erickson et al. |
| 6,371,958 B1 | 4/2002 | Overaker |
| 6,375,573 B2 | 4/2002 | Romano |
| 6,379,386 B1 | 4/2002 | Resch et al. |
| 6,409,765 B1 | 6/2002 | Bianchi et al. |
| D460,188 S | 7/2002 | Michelson |
| D460,189 S | 7/2002 | Michelson |
| 6,419,678 B1 | 7/2002 | Asfora |
| 6,419,703 B1 | 7/2002 | Fallin et al. |
| 6,436,099 B1 | 8/2002 | Drewry et al. |
| 6,436,101 B1 | 8/2002 | Hamada et al. |
| 6,436,146 B1 | 8/2002 | Hassler et al. |
| D463,560 S | 9/2002 | Michelson |
| 6,447,544 B1 | 9/2002 | Michelson |
| 6,470,207 B1 | 10/2002 | Simon et al. |
| 6,565,605 B2 | 5/2003 | Goble et al. |
| 6,572,617 B1 | 6/2003 | Senegas |
| 6,579,318 B2 | 6/2003 | Varga et al. |
| 6,579,319 B2 | 6/2003 | Goble et al. |
| 6,589,244 B1 | 7/2003 | Sevrain et al. |
| 6,600,956 B2 | 7/2003 | Maschino et al. |
| 6,607,530 B1 | 8/2003 | Carl et al. |
| 6,610,091 B1 | 8/2003 | Reiley |
| D479,331 S | 9/2003 | Pike et al. |
| 6,626,944 B1 | 9/2003 | Taylor |
| 6,641,614 B1 | 11/2003 | Wagner et al. |
| 6,656,178 B1 | 12/2003 | Veldhuizen et al. |
| 6,656,195 B2 | 12/2003 | Peters et al. |
| 6,669,697 B1 | 12/2003 | Pisharodi |
| 6,669,729 B2 | 12/2003 | Chin |
| 6,679,914 B1 | 1/2004 | Gabbay |
| 6,706,068 B2 | 3/2004 | Ferree |
| 6,743,232 B2 | 6/2004 | Overaker et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,783,527 B2 | 8/2004 | Drewry et al. |
| 6,790,210 B1 | 9/2004 | Cragg et al. |
| 6,802,863 B2 | 10/2004 | Lawson et al. |
| 6,811,567 B2 | 11/2004 | Reiley |
| 6,902,566 B2 | 6/2005 | Zucherman et al. |
| 6,908,484 B2 | 6/2005 | Zubok et al. |
| 6,966,930 B2 | 11/2005 | Arnin et al. |
| 6,974,478 B2 | 12/2005 | Reiley et al. |
| 6,974,479 B2 | 12/2005 | Trieu |
| 7,004,971 B2 | 2/2006 | Serhan et al. |
| D517,404 S | 3/2006 | Schluter |
| 7,008,429 B2 | 3/2006 | Golobek |
| 7,013,675 B2 | 3/2006 | Marquez-Pickering |
| 7,051,451 B2 | 5/2006 | Augostino et al. |
| 7,074,238 B2 | 7/2006 | Stinson et al. |
| 7,101,375 B2 | 9/2006 | Zucherman et al. |
| 7,223,269 B2 | 5/2007 | Chappuis |
| D565,180 S | 3/2008 | Schluter |
| 7,371,238 B2 | 5/2008 | Sololeski et al. |
| 7,458,981 B2 | 12/2008 | Fielding et al. |
| 7,517,358 B2 | 4/2009 | Petersen |
| 7,537,611 B2 | 5/2009 | Lee |
| 7,559,940 B2 | 7/2009 | McGuire et al. |
| 7,563,286 B2 | 7/2009 | Gerber et al. |
| 7,585,300 B2 | 9/2009 | Cha |
| 7,608,104 B2 | 10/2009 | Yuan et al. |
| 7,695,472 B2 | 4/2010 | Young |
| 7,799,077 B2 | 9/2010 | Lang et al. |
| 7,806,895 B2 | 10/2010 | Weier et al. |
| 7,846,183 B2 | 12/2010 | Blain |
| 7,862,590 B2 * | 1/2011 | Lim ................ A61B 17/7067 606/248 |
| 7,935,136 B2 | 5/2011 | Alamin et al. |
| D643,121 S | 8/2011 | Milford et al. |
| 7,993,370 B2 | 8/2011 | Jahng |
| 7,998,172 B2 | 8/2011 | Blain |
| 8,052,728 B2 | 11/2011 | Hestad |
| 8,109,971 B2 | 2/2012 | Hale |
| 8,133,225 B2 | 3/2012 | Pieske |
| 8,163,016 B2 | 4/2012 | Linares |
| 8,172,877 B2 | 5/2012 | Winslow et al. |
| 8,177,810 B2 | 5/2012 | Ferree |
| 8,192,468 B2 | 6/2012 | Biedermann et al. |
| 8,216,275 B2 | 7/2012 | Fielding et al. |
| 8,231,661 B2 | 7/2012 | Carls |
| 8,246,655 B2 | 8/2012 | Jackson et al. |
| 8,267,966 B2 | 9/2012 | McCormack et al. |
| 8,292,954 B2 | 10/2012 | Robinson et al. |
| 8,306,307 B2 | 11/2012 | Koike et al. |
| 8,382,801 B2 | 2/2013 | Lamborne et al. |
| 8,394,125 B2 | 3/2013 | Assell |
| 8,460,346 B2 | 6/2013 | Ralph et al. |
| 8,486,078 B2 | 7/2013 | Carl et al. |
| 8,496,691 B2 | 7/2013 | Blain |
| 8,579,903 B2 | 11/2013 | Carl |
| 8,652,137 B2 | 2/2014 | Blain et al. |
| 8,740,942 B2 | 6/2014 | Blain |
| 8,740,949 B2 | 6/2014 | Blain |
| 8,753,345 B2 | 6/2014 | McCormack et al. |
| 8,784,423 B2 | 7/2014 | Kowarsch et al. |
| 8,858,597 B2 | 10/2014 | Blain |
| 8,882,804 B2 | 11/2014 | Blain |
| 8,961,613 B2 | 2/2015 | Assell et al. |
| D724,733 S | 3/2015 | Blain et al. |
| 8,974,456 B2 | 3/2015 | Allen et al. |
| 8,979,529 B2 | 3/2015 | Marcus |
| 8,992,533 B2 | 3/2015 | Blain et al. |
| 8,998,953 B2 | 4/2015 | Blain |
| 9,017,389 B2 | 4/2015 | Assell et al. |
| 9,060,787 B2 | 6/2015 | Blain et al. |
| 9,101,410 B1 | 8/2015 | Urrea |

(56) References Cited

U.S. PATENT DOCUMENTS

| | | |
|---|---|---|
| D739,935 S | 9/2015 | Blain et al. |
| 9,149,283 B2 | 10/2015 | Assell et al. |
| 9,161,763 B2 | 10/2015 | Assell et al. |
| 9,179,943 B2 | 11/2015 | Blain |
| 9,220,547 B2 | 12/2015 | Blain et al. |
| D748,262 S | 1/2016 | Blain |
| 9,233,006 B2 | 1/2016 | Assell et al. |
| D748,793 S | 2/2016 | Blain |
| 9,265,546 B2 | 2/2016 | Blain |
| 9,271,765 B2 | 3/2016 | Blain |
| 9,301,786 B2 | 4/2016 | Blain |
| 9,314,277 B2 | 4/2016 | Assell et al. |
| 9,345,488 B2 | 5/2016 | Assell et al. |
| 9,421,044 B2 | 8/2016 | Blain et al. |
| D765,853 S | 9/2016 | Blain et al. |
| D765,854 S | 9/2016 | Blain et al. |
| 9,456,855 B2 | 10/2016 | Blain et al. |
| 9,517,077 B2 | 12/2016 | Blain et al. |
| D777,921 S | 1/2017 | Blain et al. |
| D780,315 S | 2/2017 | Blain et al. |
| 9,572,602 B2 | 2/2017 | Blain et al. |
| 9,615,861 B2 | 4/2017 | Perez-Cruet et al. |
| D790,062 S | 6/2017 | Blain et al. |
| 9,675,387 B2 | 6/2017 | Blain |
| 9,743,937 B2 | 8/2017 | Blain et al. |
| 9,808,294 B2 | 11/2017 | Blain |
| 9,820,784 B2 | 11/2017 | Blain et al. |
| 9,839,450 B2 | 12/2017 | Blain et al. |
| D810,942 S | 2/2018 | Blain et al. |
| D812,754 S | 3/2018 | Blain et al. |
| 9,936,984 B2 | 4/2018 | Blain |
| 10,022,161 B2 | 7/2018 | Blain |
| 10,085,776 B2 | 10/2018 | Blain |
| D834,194 S | 11/2018 | Blain et al. |
| 10,194,955 B2 | 2/2019 | Blain et al. |
| 10,251,679 B2 | 4/2019 | Blain et al. |
| D857,900 S | 8/2019 | Blain et al. |
| 10,368,921 B2 | 8/2019 | Blain |
| 10,426,524 B2 | 10/2019 | Blain |
| 10,624,680 B2 | 4/2020 | Blain |
| D884,896 S | 5/2020 | Blain et al. |
| 10,758,361 B2 | 9/2020 | Blain |
| D926,982 S | 8/2021 | Blain et al. |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0120335 A1 | 8/2002 | Angelucci et al. |
| 2002/0123806 A1 | 9/2002 | Reiley |
| 2002/0138077 A1 | 9/2002 | Ferree |
| 2002/0151895 A1 | 10/2002 | Soboleski et al. |
| 2002/0173800 A1 | 11/2002 | Dreyfuss et al. |
| 2002/0173813 A1 | 11/2002 | Peterson et al. |
| 2002/0198527 A1 | 12/2002 | Muckter |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0093152 A1 | 5/2003 | Pedersen et al. |
| 2003/0093154 A1 | 5/2003 | Estes et al. |
| 2003/0120343 A1 | 6/2003 | Whelan |
| 2003/0176919 A1 | 9/2003 | Schmieding |
| 2003/0176922 A1 | 9/2003 | Lawson et al. |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0087954 A1 | 5/2004 | Allen et al. |
| 2004/0116927 A1 | 6/2004 | Graf |
| 2004/0127989 A1 | 7/2004 | Dooris et al. |
| 2004/0143264 A1 | 7/2004 | McAfee |
| 2004/0176844 A1 | 9/2004 | Zubok et al. |
| 2004/0195727 A1 | 10/2004 | Stoy |
| 2004/0199166 A1 | 10/2004 | Schmieding et al. |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0107879 A1 | 5/2005 | Christensen et al. |
| 2005/0131409 A1 | 6/2005 | Chervitz et al. |
| 2005/0131538 A1 | 6/2005 | Chervitz et al. |
| 2005/0143818 A1 | 6/2005 | Yuan et al. |
| 2005/0154463 A1 | 7/2005 | Trieu |
| 2005/0159746 A1 | 7/2005 | Grab et al. |
| 2005/0197700 A1 | 9/2005 | Boehem et al. |
| 2005/0204515 A1 | 9/2005 | Hewes |
| 2005/0216017 A1 | 9/2005 | Fielding et al. |
| 2005/0240201 A1 | 10/2005 | Yeung |
| 2005/0251256 A1 | 11/2005 | Reiley |
| 2005/0256494 A1 | 11/2005 | Datta |
| 2006/0004367 A1 | 1/2006 | Alamin et al. |
| 2006/0036323 A1 | 2/2006 | Carl et al. |
| 2006/0041311 A1 | 2/2006 | McLeer |
| 2006/0084985 A1 | 4/2006 | Kim |
| 2006/0085006 A1 | 4/2006 | Ek et al. |
| 2006/0085072 A1 | 4/2006 | Funk et al. |
| 2006/0111782 A1 | 5/2006 | Petersen |
| 2006/0116684 A1 | 6/2006 | Whelan |
| 2006/0149289 A1 | 7/2006 | Winslow et al. |
| 2006/0149375 A1 | 7/2006 | Yuan et al. |
| 2006/0200137 A1 | 9/2006 | Soboleski et al. |
| 2006/0241597 A1 | 10/2006 | Mitchell et al. |
| 2006/0241601 A1 | 10/2006 | Trautwein et al. |
| 2006/0241758 A1 | 10/2006 | Peterman et al. |
| 2006/0241778 A1 | 10/2006 | Ogilvie |
| 2006/0247650 A1 | 11/2006 | Yerby et al. |
| 2006/0293691 A1 | 12/2006 | Mitra et al. |
| 2007/0055236 A1 | 3/2007 | Hudgins et al. |
| 2007/0055252 A1 | 3/2007 | Blain et al. |
| 2007/0055373 A1 | 3/2007 | Hudgins et al. |
| 2007/0078464 A1 | 4/2007 | Jones et al. |
| 2007/0100452 A1 | 5/2007 | Prosser |
| 2007/0118218 A1 | 5/2007 | Hooper |
| 2007/0123863 A1 | 5/2007 | Winslow et al. |
| 2007/0135814 A1 | 6/2007 | Farris |
| 2007/0149976 A1 | 6/2007 | Hale et al. |
| 2007/0179619 A1 | 8/2007 | Grab |
| 2007/0250166 A1 | 10/2007 | McKay |
| 2007/0270812 A1 | 11/2007 | Peckham |
| 2008/0009866 A1 | 1/2008 | Alamin et al. |
| 2008/0046083 A1 | 2/2008 | Hewko |
| 2008/0058929 A1 | 3/2008 | Whelan |
| 2008/0082103 A1 | 4/2008 | Hutton et al. |
| 2008/0161853 A1 | 7/2008 | Arnold et al. |
| 2008/0177264 A1 | 7/2008 | Alamin et al. |
| 2008/0177326 A1 | 7/2008 | Thompson |
| 2008/0183209 A1 | 7/2008 | Robinson et al. |
| 2008/0183211 A1 | 7/2008 | Lamborne et al. |
| 2008/0228225 A1 | 9/2008 | Trautwein et al. |
| 2008/0255664 A1 | 10/2008 | Hogendijk et al. |

(56) References Cited

U.S. PATENT DOCUMENTS

| | | |
|---|---|---|
| 2008/0262549 A1 | 10/2008 | Bennett et al. |
| 2008/0287996 A1 | 11/2008 | Soholeski et al. |
| 2009/0005818 A1 | 1/2009 | Chin et al. |
| 2009/0005873 A1 | 1/2009 | Slivka et al. |
| 2009/0018662 A1 | 1/2009 | Pasquet et al. |
| 2009/0024166 A1 | 1/2009 | Carl et al. |
| 2009/0036926 A1 | 2/2009 | Hestad |
| 2009/0072006 A1 | 3/2009 | Clauson et al. |
| 2009/0076617 A1 | 3/2009 | Ralph et al. |
| 2009/0105766 A1 | 4/2009 | Thompson et al. |
| 2009/0125066 A1 | 5/2009 | Kraus et al. |
| 2009/0138048 A1 | 5/2009 | Baccelli et al. |
| 2009/0171360 A1 | 7/2009 | Whelan |
| 2009/0198282 A1 | 8/2009 | Fielding et al. |
| 2009/0248077 A1 | 10/2009 | Johns |
| 2009/0248082 A1 | 10/2009 | Crook et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2009/0270929 A1 | 10/2009 | Suddaby |
| 2009/0306716 A1 | 12/2009 | Beger et al. |
| 2009/0326589 A1 | 12/2009 | Lemoine et al. |
| 2010/0010548 A1 | 1/2010 | Hermida Ochoa |
| 2010/0063550 A1 | 3/2010 | Felix et al. |
| 2010/0076503 A1 | 3/2010 | Beyar et al. |
| 2010/0087859 A1 | 4/2010 | Jackson, Jr. |
| 2010/0131008 A1 | 5/2010 | Overes et al. |
| 2010/0168864 A1 | 7/2010 | White et al. |
| 2010/0179553 A1 | 7/2010 | Ralph et al. |
| 2010/0185241 A1 | 7/2010 | Malandain et al. |
| 2010/0191286 A1 | 7/2010 | Butler |
| 2010/0204700 A1 | 8/2010 | Falahee |
| 2010/0204732 A1 | 8/2010 | Aschmann et al. |
| 2010/0234894 A1 | 9/2010 | Alamin et al. |
| 2010/0274289 A1 | 10/2010 | Carls et al. |
| 2010/0292698 A1 | 11/2010 | Hulliger et al. |
| 2010/0298829 A1 | 11/2010 | Schaller et al. |
| 2010/0318133 A1 | 12/2010 | Tornier |
| 2011/0015744 A1 | 1/2011 | Squires et al. |
| 2011/0022050 A1 | 1/2011 | McClellan et al. |
| 2011/0022089 A1 | 1/2011 | Assell et al. |
| 2011/0034956 A1 | 2/2011 | Mazda et al. |
| 2011/0040301 A1 | 2/2011 | Blain et al. |
| 2011/0060366 A1 | 3/2011 | Heim et al. |
| 2011/0082503 A1 | 4/2011 | Blain |
| 2011/0098816 A1 | 4/2011 | Jacob et al. |
| 2011/0106163 A1* | 5/2011 | Hochschuler ...... A61B 17/7071 606/264 |
| 2011/0160772 A1 | 6/2011 | Arcenio et al. |
| 2011/0172712 A1 | 7/2011 | Chee et al. |
| 2011/0245875 A1 | 10/2011 | Karim |
| 2011/0295318 A1 | 12/2011 | Alamin et al. |
| 2011/0301644 A1 | 12/2011 | Belliard |
| 2011/0313456 A1 | 12/2011 | Blain |
| 2012/0022591 A1 | 1/2012 | Baccelli et al. |
| 2012/0022649 A1 | 1/2012 | Robinson et al. |
| 2012/0035658 A1 | 2/2012 | Goble et al. |
| 2012/0041441 A1 | 2/2012 | Bernstein et al. |
| 2012/0046749 A1 | 2/2012 | Tatsumi |
| 2012/0101502 A1 | 4/2012 | Kartalian et al. |
| 2012/0150231 A1 | 6/2012 | Alamin et al. |
| 2012/0221048 A1 | 8/2012 | Blain |
| 2012/0221049 A1 | 8/2012 | Blain |
| 2012/0221060 A1 | 8/2012 | Blain |
| 2012/0245586 A1 | 9/2012 | Lehenkari et al. |
| 2012/0271354 A1 | 10/2012 | Baccelli et al. |
| 2012/0277801 A1 | 11/2012 | Marik et al. |
| 2012/0310244 A1 | 12/2012 | Blain et al. |
| 2013/0023878 A1 | 1/2013 | Belliard et al. |
| 2013/0041410 A1 | 2/2013 | Hestad et al. |
| 2013/0079778 A1 | 3/2013 | Azuero et al. |
| 2013/0123923 A1 | 5/2013 | Pavlov et al. |
| 2013/0197643 A1 | 8/2013 | Greenberg et al. |
| 2013/0204250 A1 | 8/2013 | McDevitt et al. |
| 2013/0245693 A1 | 9/2013 | Blain |
| 2013/0253649 A1 | 9/2013 | Davis |
| 2013/0261625 A1 | 10/2013 | Koch et al. |
| 2013/0325065 A1 | 12/2013 | Malandain et al. |
| 2014/0012318 A1 | 1/2014 | Goel |
| 2014/0018816 A1 | 1/2014 | Fenn et al. |
| 2014/0066758 A1 | 3/2014 | Marik et al. |
| 2014/0214084 A1 | 7/2014 | Jackson et al. |
| 2014/0228883 A1 | 8/2014 | Blain |
| 2014/0257397 A1 | 9/2014 | Akbarnia et al. |
| 2014/0277142 A1 | 9/2014 | Blain et al. |
| 2014/0277149 A1 | 9/2014 | Rooney et al. |
| 2014/0309699 A1 | 10/2014 | Houff |
| 2014/0336653 A1 | 11/2014 | Bromer |
| 2014/0378976 A1 | 12/2014 | Garcia |
| 2015/0045794 A1 | 2/2015 | Garcia et al. |
| 2015/0081023 A1 | 3/2015 | Blain |
| 2015/0094766 A1 | 4/2015 | Blain et al. |
| 2015/0094767 A1 | 4/2015 | Blain et al. |
| 2015/0119988 A1 | 4/2015 | Assell et al. |
| 2015/0164516 A1 | 6/2015 | Blain et al. |
| 2015/0164652 A1 | 6/2015 | Assell et al. |
| 2015/0190149 A1 | 7/2015 | Assell et al. |
| 2015/0196330 A1 | 7/2015 | Blain |
| 2015/0209096 A1 | 7/2015 | Gephart |
| 2015/0257770 A1 | 9/2015 | Assell et al. |
| 2015/0257773 A1 | 9/2015 | Blain et al. |
| 2015/0327872 A1 | 11/2015 | Assell et al. |
| 2015/0342648 A1 | 12/2015 | McCormack et al. |
| 2016/0051294 A1 | 2/2016 | Blain |
| 2016/0113692 A1 | 4/2016 | Knoepfle |
| 2016/0128739 A1 | 5/2016 | Blain et al. |
| 2016/0128838 A1 | 5/2016 | Assell et al. |
| 2016/0213481 A1 | 7/2016 | Blain |
| 2016/0324549 A1 | 11/2016 | Blain |
| 2017/0000527 A1 | 1/2017 | Blain et al. |
| 2017/0105767 A1 | 4/2017 | Blain |
| 2017/0239060 A1 | 8/2017 | Blain |
| 2017/0281232 A1 | 10/2017 | Smith |
| 2017/0296234 A1 | 10/2017 | Jackson et al. |
| 2017/0333091 A1 | 11/2017 | Taber et al. |
| 2018/0049780 A1 | 2/2018 | Blain |
| 2018/0085148 A1 | 3/2018 | Blain |
| 2018/0085149 A1 | 3/2018 | Blain |
| 2019/0142478 A1 | 5/2019 | Blain |
| 2019/0328428 A1 | 10/2019 | Blain |
| 2019/0365433 A1 | 12/2019 | Blain et al. |
| 2020/0000608 A1 | 1/2020 | Bullard et al. |
| 2020/0214746 A1 | 7/2020 | Blain et al. |
| 2020/0367945 A1 | 11/2020 | Semingson et al. |
| 2021/0121207 A1 | 4/2021 | Semingson |

FOREIGN PATENT DOCUMENTS

| | | |
|---|---|---|
| DE | 201 12 123 | 9/2001 |
| DE | 101 35 771 | 2/2003 |
| EP | 0 238 219 | 9/1987 |
| EP | 0 322 334 | 6/1989 |
| EP | 0 392 124 | 10/1990 |
| EP | 0 610 837 | 8/1994 |
| EP | 0 928 603 | 7/1999 |
| EP | 1 201 202 | 5/2002 |
| EP | 1 201 256 | 5/2002 |
| EP | 2 138 122 | 12/2009 |
| EP | 2 813 190 | 12/2014 |
| EP | 2 919 717 | 9/2015 |
| FR | 2 704 745 | 11/1994 |
| FR | 2 722 980 | 2/1996 |
| GB | 2 366 736 | 3/2002 |
| JP | 53-005889 | 1/1978 |
| JP | 62-270147 | 11/1987 |
| JP | 03-100154 | 4/1991 |
| JP | 03-240660 | 10/1991 |
| JP | 08-509918 | 10/1996 |
| JP | 10-179622 | 7/1998 |
| JP | 2000-201941 | 7/2000 |
| JP | 2000-210297 | 8/2000 |
| JP | 2003-079649 | 3/2003 |
| JP | 2004-508888 | 3/2004 |
| JP | 2004-181236 | 7/2004 |

(56) References Cited

FOREIGN PATENT DOCUMENTS

| | | |
|---|---|---|
| JP | 2004-537354 | 12/2004 |
| JP | 2006-230722 | 9/2006 |
| JP | 2006-528540 | 12/2006 |
| JP | 2007-503884 | 3/2007 |
| JP | 2007-517627 | 7/2007 |
| JP | 2007-190389 | 8/2007 |
| JP | 2007-521881 | 8/2007 |
| JP | 2008-510526 | 4/2008 |
| JP | 2008-522787 | 7/2008 |
| JP | 2008-537498 | 9/2008 |
| JP | 2009-533167 | 9/2009 |
| JP | 2010-510852 | 4/2010 |
| JP | 2010-173739 | 8/2010 |
| JP | 2012-509740 | 4/2012 |
| JP | 2012-521221 | 9/2012 |
| JP | 2013-534451 | 9/2013 |
| JP | 2013-535247 | 9/2013 |
| JP | 2014-513583 | 6/2014 |
| MX | 6012309 | 1/2007 |
| WO | WO-8806022 A1 * 8/1988 ............ A61B 17/823 |
| WO | WO 93/014721 | 8/1993 |
| WO | WO 94/004088 | 3/1994 |
| WO | WO 97/047246 | 12/1997 |
| WO | WO 98/048717 | 11/1998 |
| WO | WO 99/023963 | 5/1999 |
| WO | WO 00/038582 | 7/2000 |
| WO | WO 00/053126 | 9/2000 |
| WO | WO 01/030248 | 5/2001 |
| WO | WO 02/045765 | 6/2002 |
| WO | WO 02/065954 | 8/2002 |
| WO | WO 02/096300 | 12/2002 |
| WO | WO 03/101350 | 12/2003 |
| WO | WO 2004/071358 | 8/2004 |
| WO | WO 2005/020850 | 3/2005 |
| WO | WO 2005/072661 | 8/2005 |
| WO | WO 2006/023980 | 3/2006 |
| WO | WO 2006/096803 | 9/2006 |
| WO | WO 2008/008522 | 1/2008 |
| WO | WO 2009/013397 | 1/2009 |
| WO | WO 2009/015100 | 1/2009 |
| WO | WO 2009/021876 | 2/2009 |
| WO | WO 2010/060072 | 5/2010 |
| WO | WO 2010/122472 | 10/2010 |
| WO | WO 2011/011621 | 1/2011 |
| WO | WO 2012/007941 | 1/2012 |
| WO | WO 2012/024162 | 2/2012 |
| WO | WO 2012/116266 | 8/2012 |
| WO | WO 2012/116267 | 8/2012 |
| WO | WO 2012/154265 | 11/2012 |
| WO | WO 2013/022880 | 2/2013 |
| WO | WO 2013/138655 | 9/2013 |
| WO | WO 2014/078541 | 5/2014 |
| WO | WO 2014/158690 | 10/2014 |
| WO | WO 2014/158695 | 10/2014 |
| WO | WO 2015/047909 | 4/2015 |
| WO | WO 2016/044432 | 3/2016 |
| WO | WO 2020/236229 | 11/2020 |
| WO | WO 2021/163313 | 8/2021 |

OTHER PUBLICATIONS

ArthroTek, "CurvTek® Bone Tunneling System," Surgical Technique, 2000, pp. 6.
ArthroTek, "CurvTek® Bone Tunneling System," User's Manual, 2000, pp. 20.
Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.
Beaman, MD et al., "Substance P Innervation of Lumbar Spine Facet Joints", Spine, 1993, vol. 18, No. 8, pp. 1044-1049.
Butterman, et al., "An Experimental Method for Measuring Force on the Spinal Facet Joint: Description and Application of the Method", Journal of Biomechanical Engineering, Nov. 1991, vol. 113, pp. 375-386.
Cruess et al., "The Response of Articular Cartilage to Weight-Bearing Against Metal", The Journal of Bone and Joint Surgery, Aug. 1984, vol. 66-B, No. 4, pp. 592-597.
Dalldorf et al., "Rate of Degeneration of Human Acetabular Cartilage after Hemiarthroplasty", The Journal of Bone and Joint Surgery, Jun. 1995, vol. 77. No. 6, pp. 877-882.
E-mail from 3rd Party citing U.S. Appl. Nos. 60/721,909; 60/750,005 and 60/749,000, initial e-mail dated May 11, 2009, reply e-mail dated May 18, 2009.
Frost, Harold M., "From Wolff's Law to the Utah Paradigm: Insights About Bone Physiology and Its Clinical Applications", The Anatomical Record, 2001, vol. 262, pp. 398-419.
King et al., "Mechanism of Spinal Injury Due to Caudocephalad Acceleration," Symposium on the Lumbar Spine, Orthopedic Clinic of North America, Jan. 1975, vol. 6, pp. 19-31.
Kurtz, PhD et al., "Isoelastic Polyaryletheretherketone Implants for Total Joint Replacement", PEEK Biomaterials Handbook, Ch. 14, 2012, pp. 221-226.
Meisel et al., "Minimally Invasive Facet Restoration Implant for Chronic Lumbar Zygapophysial Pain: 1-Year Outcomes", Annals of Surgical Innovation and Research (ASIR), 2014, vol. 8, No. 7, pp. 6.
Panjabi, PhD et al., "Articular Facets of the Human Spine: Quantitative Three-Dimensional Anatomy", Spine, 1993, vol. 18, No. 10, pp. 1298-1310.
PARTEQ Innovations, "Facet Joint Implants & Resurfacing Devices," Technology Opportunity Bulletin, Tech ID 1999-012, Queen's University, Ontario Canada, pp. 2.
Ravikumar et al., "Internal Fixation Versus Hemiarthroplasty Versus Total Hip Arthroplasty for Displaced Subcapital Fractures of Femur—13 year Results of a Prospective Randomised Study", International Journal of the Care of the Injured (INJURY), 2000, vol. 31, pp. 793-797.
Schendel et al., "Experimental Measurement of Ligament Force, Facet Force, and Segment Motion in the Human Lumbar Spine", Journal of Biomechanics, 1993, vol. 26, No. 4/5, pp. 427-438.
Sharpe Products, "Metal Round Disks", https://web.archive.org/web/20170705214756/https://sharpeproducts.com/store/metal-round-disks, as archived Jul. 5, 2017 in 3 pages.
Tanno et al., "Which Portion in a Facet is Specifically Affected by Articular Cartilage Degeneration with Aging in the Human Lumbar Zygapophysial Joint?", Okajimas Folia Anatomica Japonica, May 2003, vol. 80, No. 1, pp. 29-34.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.
Official Communication in Australian Application No. AU2013237744, dated Sep. 2, 2014.
Notice of Acceptance in Australian Application No. AU2013237744, dated Apr. 23, 2015.
Official Communication in Australian Application No. AU2015205875, dated Apr. 2, 2016.
Official Communication in Australian Application No. AU2015205875, dated Jun. 15, 2016.
Official Communication in Australian Application No. AU2016231622, dated Dec. 5, 2017.
Official Communication in Australian Application No. AU2016231622, dated Nov. 22, 2018.
Notice of Acceptance in Australian Application No. AU2016231622, dated Dec. 4, 2018.
Official Communication in Canadian Application No. 2,555,355, dated Sep. 2, 2011.
Official Communication in Canadian Application No. 2,803,783, dated Sep. 29, 2014.

(56) References Cited

OTHER PUBLICATIONS

Official Communication in Canadian Application No. 2,803,783, dated Aug. 5, 2015.
Official Communication in Canadian Application No. 2,803,783, dated Jul. 7, 2016.
Official Communication in Canadian Application No. 2,803,783, dated Apr. 5, 2017.
Official Communication in European Application No. 05712981.9, dated Jul. 24, 2007.
Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.
Official Communication in European Application No. 14175088.5, dated Nov. 18, 2015.
Official Communication in European Application No. 16180368.9, dated Mar. 31, 2017.
Official Communication in European Application No. 16180368.9, dated Jan. 11, 2018.
Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
Official Communication in Japanese Application No. 2012-272106, dated Feb. 23, 2015.
Official Communication in Japanese Application No. 2012-272106, dated Nov. 2, 2015.
International Search Report and Written Opinion in International Application No. PCT/US2005/003753, dated Dec. 5, 2006.
International Preliminary Report and Written Opinion in International App No. PCT/US2005/003753, dated Jan. 9, 2007.
Official Communication in European Application No. 08730413.5, dated Feb. 16, 2012.
Official Communication in European Application No. 14177951.2, dated Nov. 13, 2014.
International Search Report and Written Opinion in International Application No. PCT/US2008/054607, dated Jul. 10, 2008.
International Preliminary Report on Patentability in International Application No. PCT/US2008/054607, dated Sep. 3, 2009.
Official Communication in Australian Application No. 2011292297, dated Jul. 10, 2013.
Official Communication in Australian Application No. 2014277721, dated Sep. 8, 2016.
Official Communication in Australian Application No. 2014277721, dated Jan. 9, 2017.
Official Communication in Canadian Application No. 2,804,223, dated Jun. 5, 2017.
Official Communication in Canadian Application No. 2,804,223, dated Mar. 14, 2018.
Official Communication in European Application No. 11818586.7, dated Nov. 6, 2014.
Official Communication in European Application No. 11818586.7, dated Feb. 3, 2017.
Official Communication in Japanese Application No. 2013-524882, dated Mar. 2, 2015.
Official Communication in Japanese Application No. 2013-524882, dated Nov. 16, 2015.
Official Communication in Japanese Application No. 2015-242990, dated Dec. 12, 2016.
Official Communication in Japanese Application No. 2015-242990, dated May 8, 2017.
Official Communication in Japanese Application No. 2015-242990, dated Aug. 21, 2017.
International Search Report and Written Opinion in International Application No. PCT/US2011/047432, dated Dec. 12, 2011.
International Preliminary Reporton Patentability in International Application No. PCT/US2011/047432, dated Feb. 28, 2013.
Official Communication in Australian Application No. AU2012222229, dated Aug. 21, 2015.
Official Communication in Australian Application No. AU2012222229, dated May 11, 2016.
Official Communication in Australian Application No. AU2012222230, dated Aug. 21, 2015.
Official Communication in European Application No. EP12749447.4, dated Jan. 4, 2017.
Official Communication in European Application No. EP12749447.4, dated Apr. 4, 2017.
Official Communication in European Application No. EP12749447.4, dated Nov. 14, 2018.
Official Communication in European Application No. 12749251.0, dated Jan. 4, 2017.
Official Communication in European Application No. 12749251.0, dated May 9, 2017.
Official Communication in Japanese Application No. JP 2013-555591, dated Jan. 4, 2016.
Official Communication in Japanese Application No. 2016-246368, dated Oct. 30, 2017.
Official Communication in Japanese Application No. 2016-246368, dated Jul. 2, 2018.
Official Communication in Japanese Application No. JP 2013-555592, dated Dec. 7, 2015.
Official Communication in Japanese Application No. JP 2013-555592, dated Aug. 8, 2016.
Official Communication in Japanese Application No. JP 2013-555592, dated Jan. 5, 2018.
Official Communication in Japanese Application No. 2016-237460, dated Oct. 23, 2017.
Official Communication in Japanese Application No. 2016-237460, dated Apr. 16, 2018.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 12, 2014.
Official Communication in Australian Application No. 2014241989, dated Aug. 31, 2017.
Official Communication in Australian Application No. 2014241989, dated Jun. 20, 2018.
Official Communication in Australian Application No. 2014241989, dated Aug. 17, 2018.
Official Communication in European Application No. 14774714.1, dated Oct. 21, 2016.
Official Communication in Japanese Application No. JP 2016-500490, dated Nov. 27, 2017.
Official Communication in Japanese Application No. JP 2016-500490, dated May 7, 2018.
International Search Report and Written Opinion in International Application No. PCT/US2014/019302, dated May 18, 2015.
Official Communication in Australian Application No. 2014241994, dated Oct. 30, 2017.

(56) References Cited

OTHER PUBLICATIONS

Official Communication in European Application No. 14776445.0, dated Nov. 7, 2016.
Official Communication in Japanese Application No. JP 2016-500498, dated Jan. 5, 2018.
Official Communication in Japanese Application No. JP 2016-500498, dated Jul. 2, 2018.
International Search Report and Written Opinion in International Application No. PCT/US2014/019325, dated Jun. 17, 2014.
International Preliminary Report on Patentability and Written Opinion in International Application No. PCT/US2014/019325, dated Sep. 24, 2015.
Official Communication in Australian Application No. 2014327083, dated May 31, 2018.
Official Communication in European Application No. 14850082.0, dated Aug. 31, 2016.
Official Communication in Japanese Application No. JP 2016-517392, dated Jun. 4, 2018.
International Search Report and Written Opinion in International Application No. PCT/US2014/056598, dated Dec. 29, 2014.
International Preliminary Report on Patentability and Written Opinion in International Application No. PCT/US2014/056598, dated Apr. 7, 2016.
International Search Report and Written Opinion in International Application No. PCT/US2015/050441, dated Dec. 28, 2015.
International Preliminary Report on Patentability and Written Opinion in International Application No. PCT/US2015/050441, dated Mar. 30, 2017.
Official Communication in European Application No. 16743832.4, dated Jul. 24, 2018.
International Search Report and Written Opinion in International Application No. PCT/US2016/013062, dated Mar. 16, 2016.
International Preliminary Report on Patentability and Written Opinion in International Application No. PCT/US2016/013062, dated Aug. 10, 2017.
International Search Report in International Application No. PCT/CA2002/000193 filed Feb. 15, 2002, dated Jun. 18, 2002.
International Search Report and Written Opinion in International Application No. PCT/US2004/028094, dated May 16, 2005.
International Preliminary Report on Patentability in International Application No. PCT/US2004/028094, dated Feb. 25, 2013.
International Search Report in International Application No. PCT/US2005/000987 filed Jan. 13, 2005, dated May 24, 2005.
International Preliminary Report on Patentability in International Application No. PCT/US2005/000987 filed Jan. 13, 2005, dated Jan. 17, 2006.
Official Communication in Australian Application No. 2019201539, dated Jun. 25, 2019.
Official Communication in Australian Application No. 2019201539, dated Apr. 3, 2020.
Official Communication in European Application No. 19158915.9, dated Jul. 1, 2019.
Official Communication in European Application No. 12749251.0, dated Aug. 16, 2019.
Official Communication in Australian Application No. 2018279003, dated Jan. 9, 2020.
Official Communication in Australian Application No. 2018279003, dated Sep. 18, 2020.
Official Communication in Canadian Application No. 2,903,999, dated Dec. 9, 2019.
Official Communication in Canadian Application No. 2,903,999, dated Aug. 31, 2020.
Official Communication in European Application No. 14774714.1, dated May 23, 2019.
Official Communication in Australian Application No. 2014241994, dated Jan. 31, 2020.
Official Communication in Canadian Application No. 2,904,280, dated Dec. 9, 2019.
Official Communication in Canadian Application No. 2,904,280, dated Sep. 1, 2020.
Official Communication in Japanese Application No. 2016-500498, dated Mar. 4, 2019.
Official Communication in Japanese Application No. 2016-500498, dated Aug. 9, 2019.
Official Communication in Japanese Application No. 2019-163133, dated Oct. 5, 2020.
Notice of Acceptance in Australian Application No. 2014327083, dated Apr. 3, 2019.
Official Communication in Australian Application No. 2019206045, dated Sep. 8, 2020.
Official Communication in Japanese Application No. 2016-517392, dated Apr. 22, 2019.
Official Communication in Japanese Application No. 2016-517392, dated Dec. 2, 2019.
Official Communication in Australian Application No. 2016212009, dated Sep. 6, 2019.
Official Communication in Australian Application No. 2016212009, dated May 26, 2020.
Official Communication in Australian Application No. 2016212009, dated Jul. 14, 2020.
Official Communication in Japanese Application No. 2017-557269, dated Oct. 21, 2019.
Official Communication in Japanese Application No. 2017-557269, dated Jy 13, 2020.
International Search Report and Written Opinion in International Application No. PCT/US2020/014985, dated Apr. 24, 2020.
Official Communication in Australian Application No. 2018279003, dated Jan. 12, 2021.
Official Communication in Canadian Application No. 2,923,623, dated Dec. 8, 2020.
Official Communication in European Application No. 14850082.0, dated Sep. 15, 2020.
Official Communication in Japanese Application No. 2019-236855, dated Nov. 24, 2020.
Official Communication in European Application No. 11818586.7, dated Apr. 8, 2021.
Official Communication in European Application No. EP12749447.4, dated Aug. 18, 2021.
Official Communication in Canadian Application No. 2,904,280, dated Jun. 7, 2021.
Official Communication in European Application No. 14776445.0, dated Jun. 10, 2021.
Official Communication in Japanese Application No. 2019-163133, dated Jun. 7, 2021.
Official Communication in Australian Application No. 2019206045, dated Sep. 9, 2020.
Official Communication in Australian Application No. 2019206045, dated Jul. 16, 2021.
Official Communication in Japanese Application No. 2019-236855, dated Jun. 28, 2021.
International Search Report and Written Opinion in International Application No. PCT/US2021/017643, dated Apr. 28, 2021.

* cited by examiner

APPARATUS FOR BONE STABILIZATION AND DISTRACTION AND METHODS OF USE

BACKGROUND CROSS-REFERENCE TO RELATED APPLICATIONS

The present application is a continuation of U.S. application Ser. No. 15/215,137 filed on Jul. 20, 2016, which is a divisional of U.S. application Ser. No. 13/804,521 filed on Mar. 14, 2013, the disclosures of each of these applications is incorporated by reference herein in their entireties.

BACKGROUND

Some embodiments described herein relate generally to methods and apparatus for stabilizing bone, for example, stabilizing vertebrae by securing the articular processes of the vertebrae.

Traumatic, inflammatory, and degenerative disorders of the spine can lead to severe pain and loss of mobility. One source of back and spine pain is related to degeneration of the facets of the spine or facet arthritis. Bony contact or grinding of degenerated facet joint surfaces can play a role in some pain syndromes. While many technological advances have focused on the intervertebral disc and artificial replacement or repair of the intervertebral disc, relatively little advancement in facet repair has been made. Facet joint and disc degeneration frequently occur together.

The current standard of care to address the degenerative problems with the facet joints is to fuse the two adjacent vertebrae. By performing this surgical procedure, the relative motion between the two adjacent vertebrae is stopped, thus stopping motion of the facets and any potential pain generated as a result thereof. Procedures to fuse two adjacent vertebrae often involve fixation and/or stabilization of the two adjacent vertebrae until the two adjacent vertebrae fuse.

Injuries and/or surgical procedure on and/or effecting other bones can also result in the desire to fixate and/or stabilize a bone until the bone, or bone portions, can fuse, for example, to stabilize a sternum after heart surgery, to stabilize a rib after a break, etc. Current procedures to fixate and/or stabilize adjacent vertebrae and/or other bones, however, can be slow and/or complex.

Accordingly, a need exists for an apparatus and methods to better stabilize and/or fixate a bone.

SUMMARY

In some embodiments, a method includes disposing a flexible band through an aperture of a support member, the support member having a fixation portion configured to secure the support member to a first bone portion. The method includes advancing a portion of the flexible band through an attachment portion of the flexible band until the flexible band is secured to a second bone portion. The method includes advancing a portion of the fixation portion of the support member into the first bone portion until the support member is secured to the first bone portion.

DETAILED DESCRIPTION

Figure 1:
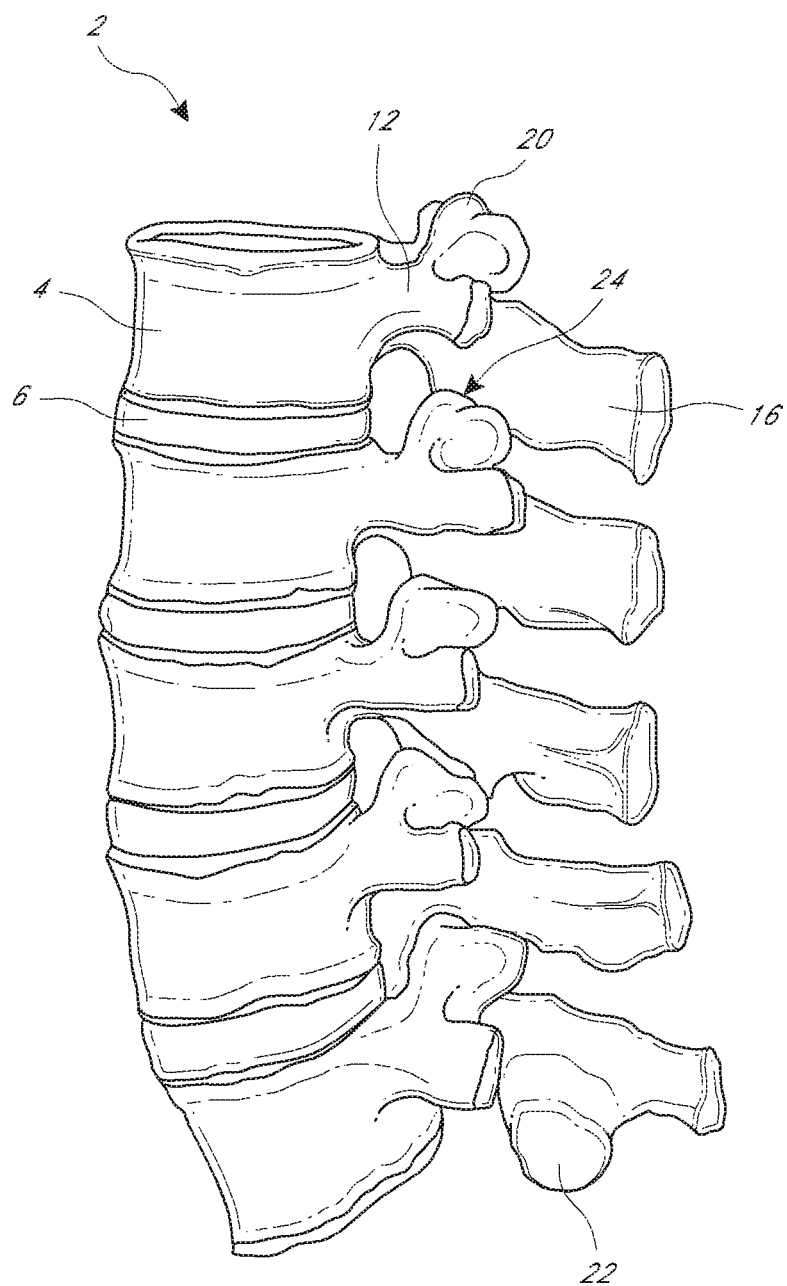
FIG. 1 is a lateral elevational view of a portion of the vertebral column.

In some embodiments, a method includes disposing a flexible band through an aperture of a support member, the support member having a fixation portion configured to secure the support member to a first bone portion. The method includes advancing a portion of the flexible band through an attachment portion of the flexible band until the flexible band is secured to a second bone portion. The method includes advancing a portion of the fixation portion of the support member into the first bone portion until the support member is secured to the first bone portion.

In some embodiments, a method includes disposing a first flexible band through a first aperture of a support member and disposing a second flexible band through a second aperture of the support member. The method includes advancing a portion of the first flexible band through an attachment portion of the first flexible band until the first flexible band is secured to a first bone portion. The method includes advancing a portion of the second flexible band through an attachment portion of the second flexible band until the second flexible band is secured to a second bone portion.

In some embodiments, an apparatus includes a flexible elongate body including a distal end portion, a body portion, and an attachment portion that is configured to receive the distal end portion. The apparatus includes a support member including (1) a first portion that includes an aperture configured to receive the distal end portion of the first flexible elongate body; and (2) a second portion configured to be coupled to a bone portion.

In some embodiments, an apparatus includes a flexible elongate body including a distal end portion, a body portion, and an attachment portion that is configured to receive the distal end portion. The apparatus includes a support member including (1) an aperture configured to receive the distal end portion of the flexible elongate body, and (2) a fixation portion configured to secure the support member to a first bone portion. The attachment portion configured to receive the distal end portion of the flexible elongate body when the body portion of the flexible elongate body is surrounds a second bone portion.

In some embodiments, a kit includes a flexible band configured to be secured to a first bone portion. The kit includes a support member having an interface portion configured to receive at least a portion of the flexible band, the support member having a fixation portion configured to secure the support member to a second bone portion such that the first bone portion and the second bone portion are stabilized.

As used in this specification, the singular forms "a," "an" and "the" include plural referents unless the context clearly dictates otherwise. Thus, for example, the term "a ratchet" is intended to mean a single ratchet or multiple ratchets. As used in this specification, a substance can include any biologic and/or chemical substance, including, but not limited to, medicine, adhesives, etc. While exemplary references are made with respect to vertebra, in some embodiments another bone can be involved. While specific reference may be made to a specific vertebra, a subset of vertebrae, and/or a grouping of vertebrae, it is understood that any vertebra, subset, and/or grouping, or combination of vertebrae can be used.

The words "proximal" and "distal" generally refer to the direction closer to and away from, respectively, a center of a body. The embodiments described herein, however, can be arranged in any orientation relative to the center of the body. Thus, when discussing the embodiments described herein (specifically a flexible elongate body), the terms "proximal" and "distal" refer to a direction closer to and away from, respectively, an attachment connection or fastener mechanism, for example, the position of which is visually presented with respect to specific embodiments in the attached figures.

Figure 2A:
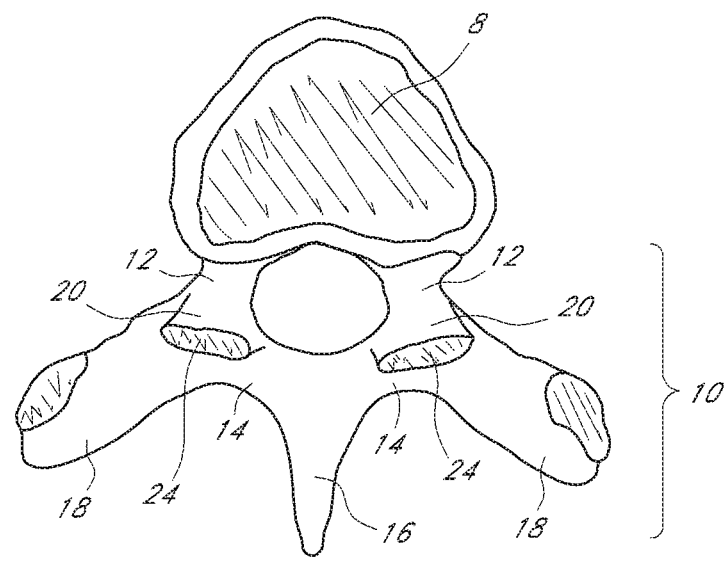
FIG. 2A is an example of a superior view of an isolated thoracic vertebra.
Figure 2B:
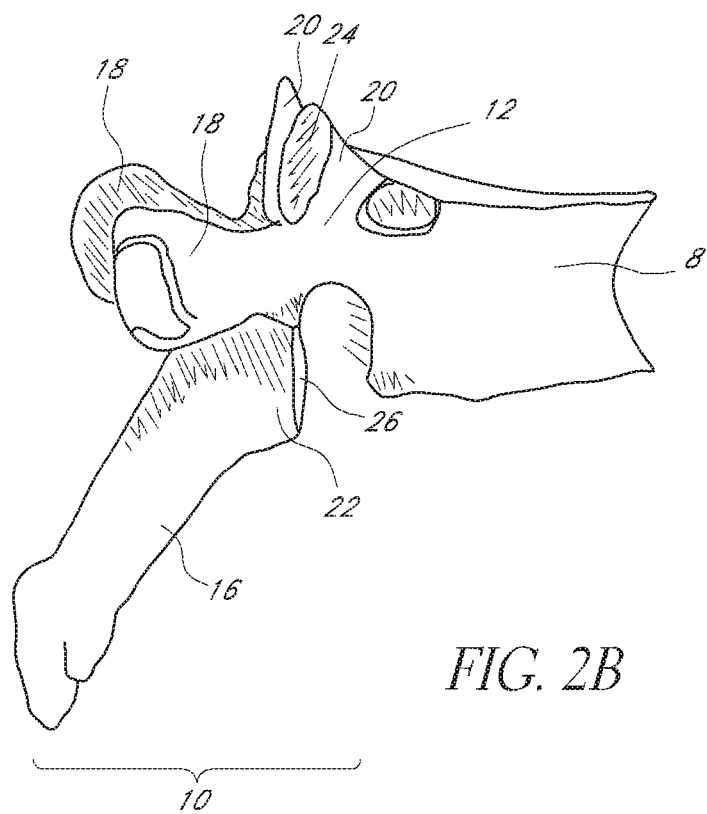
FIG. 2B is an example of a side view of an isolated thoracic vertebra.
Figure 3A:
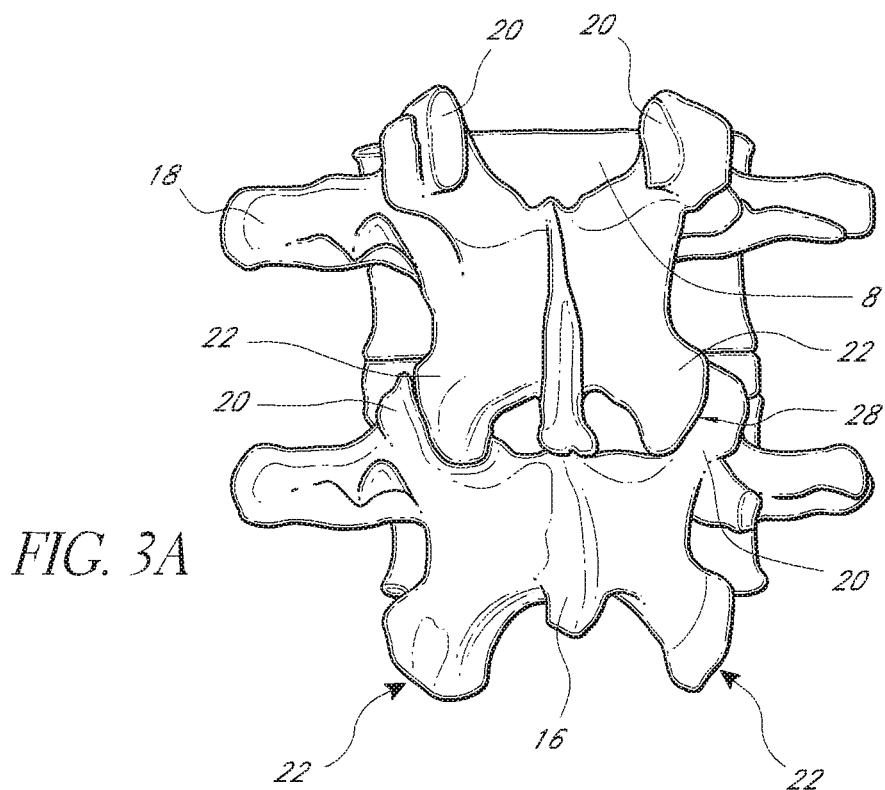
FIG. 3A is an example of a posterior elevational view of a portion of the vertebral column.
Figure 3B:
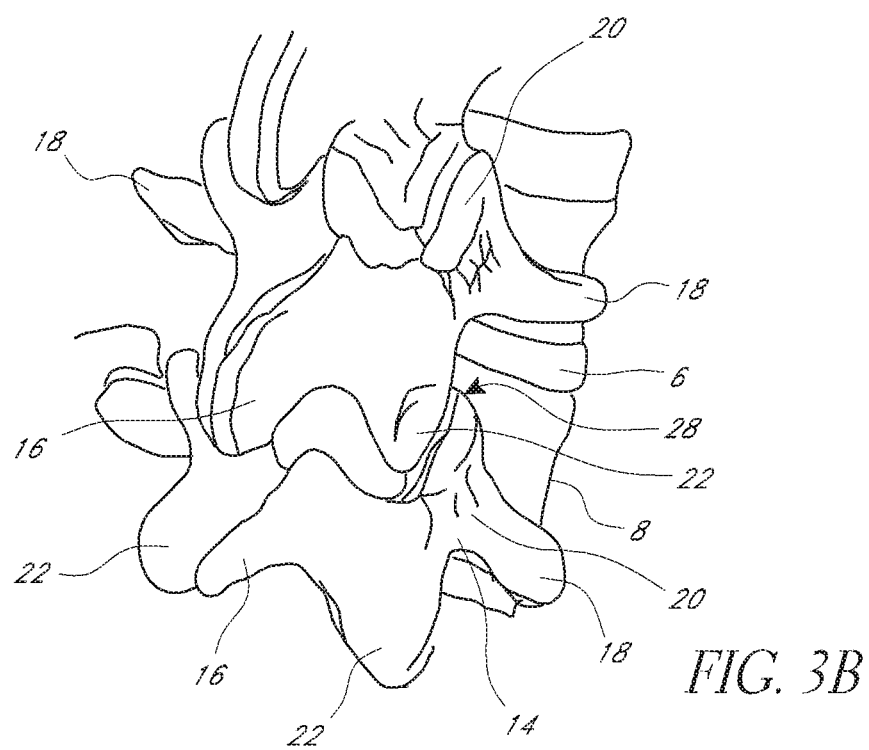
FIG. 3B is an example of a posterior-oblique elevational view of a portion of the vertebral column.
Figure 4A:
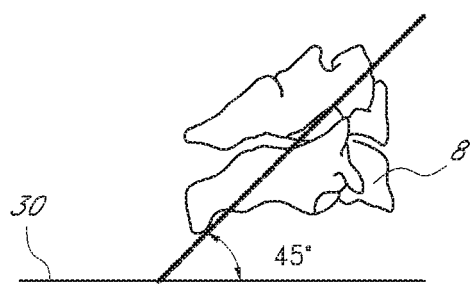
FIG. 4A is an example of a side view of a facet joint in the cervical vertebrae.
Figure 4B:
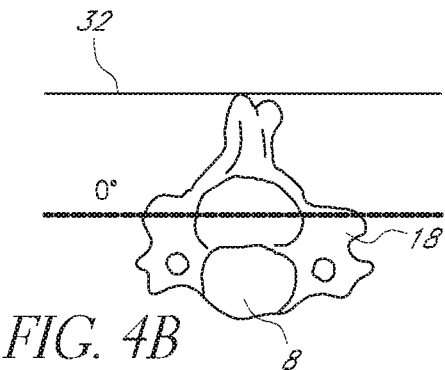
FIG. 4B is an example of a superior view of a facet joint in the cervical vertebrae.

As shown in FIG. 1, the vertebral column 2 includes a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 includes two pedicles 12 and two laminae 14. The two laminae 14 join posteriorly to form a spinous process 16. Projecting from each side of the posterior arch 10 is a transverse process 18, a superior process 20, and an inferior articular process 22. The facets 24, 26 of the superior processes 20 and the inferior articular processes 22 form facet joints 28 with the articular processes of the adjacent vertebrae (see FIGS. 3A and 3B). The facet joints are synovial joints with cartilaginous surfaces and a joint capsule.

Figure 5A:
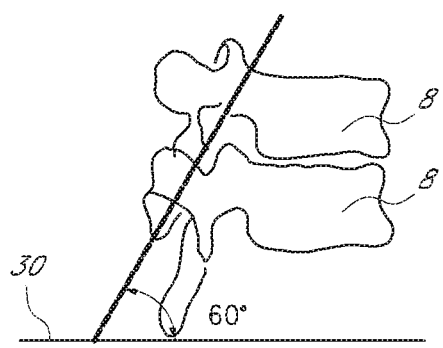
FIG. 5A is an example of a side view of a facet joint in the thoracic vertebrae.
Figure 5B:
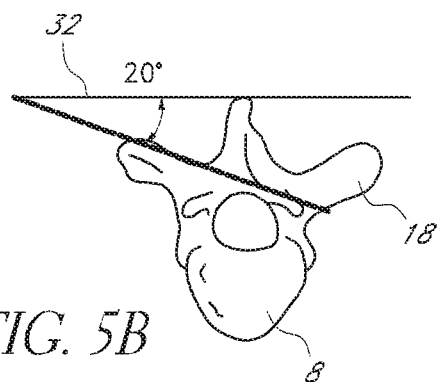
FIG. 5B is an example of a superior view of a facet joint in the thoracic vertebrae.
Figure 6A:
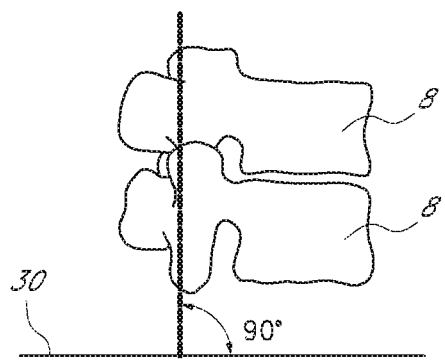
FIG. 6A is an example of a side view of a facet joint in the lumbar vertebrae.
Figure 6B:
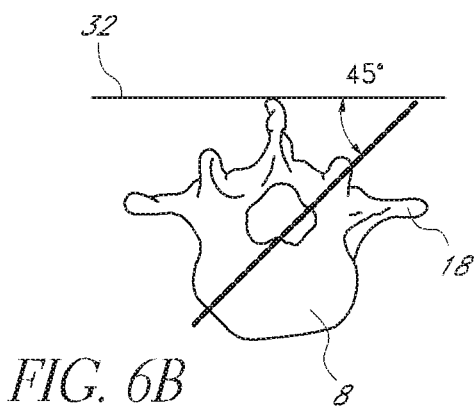
FIG. 6B is an example of a superior view of a facet joint in the lumbar vertebrae.

The orientation of the facet joints vary, depending on the level of the vertebral column. In the C1 and C2 vertebrae, for example the facet joints are parallel to the transverse plane. FIGS. 4A to 6B depict examples of the orientations of the facet joints at different levels of the vertebral column. In the C3 to C7 vertebrae examples shown in FIGS. 4A and 4B, the facets are oriented at a 45-degree angle to the transverse plane 30 and parallel to the frontal plane 32, respectively. This orientation allows the facet joints of the cervical vertebrae to flex, extend, lateral flex and rotate. At a 45-degree angle in the transverse plane 30, the facet joints of the cervical spine can guide, but do not limit, the movement of the cervical vertebrae. FIGS. 5A and 5B depict examples of the thoracic vertebrae, where the facets are oriented at a 60-degree angle to the transverse plane 30 and a 20-degree angle to the frontal plane 32, respectively. This orientation is capable of providing lateral flexion and rotation, but only limited flexion and extension. FIGS. 6A and 6B illustrate examples of the lumbar region, where the facet joints are oriented at 90-degree angles to the transverse plane 30 and a 45-degree angle to the frontal plane 32, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, Orthop. Clin. North Am., 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

In some embodiments described herein, a bone stabilization and distraction apparatus can be used to stabilize and/or fixate a first vertebra to a second vertebra, and/or distract a first vertebra relative to a second vertebra, to reduce the pain, to reduce further degradation of a spine (e.g., a specific vertebra and/or a specific disc of a spine), and/or until the first vertebra and the second vertebra have fused. In some embodiments described herein, a bone stabilization and distraction apparatus can be used in conjunction with a bone fusion procedure, for example, in conjunction with a fusion cage and/or bone cement. In such embodiments, the bone stabilization and distraction apparatus can stabilize one or more bones and/or maintain a distraction between one or more bones while the bone fusion process takes place. The bone stabilization and distraction apparatus and methods described herein can include a bone distraction tool, for example, to define an initial and/or final distraction between one or more bones prior to or during installation of a bone stabilization and distraction apparatus.

Figure 7:
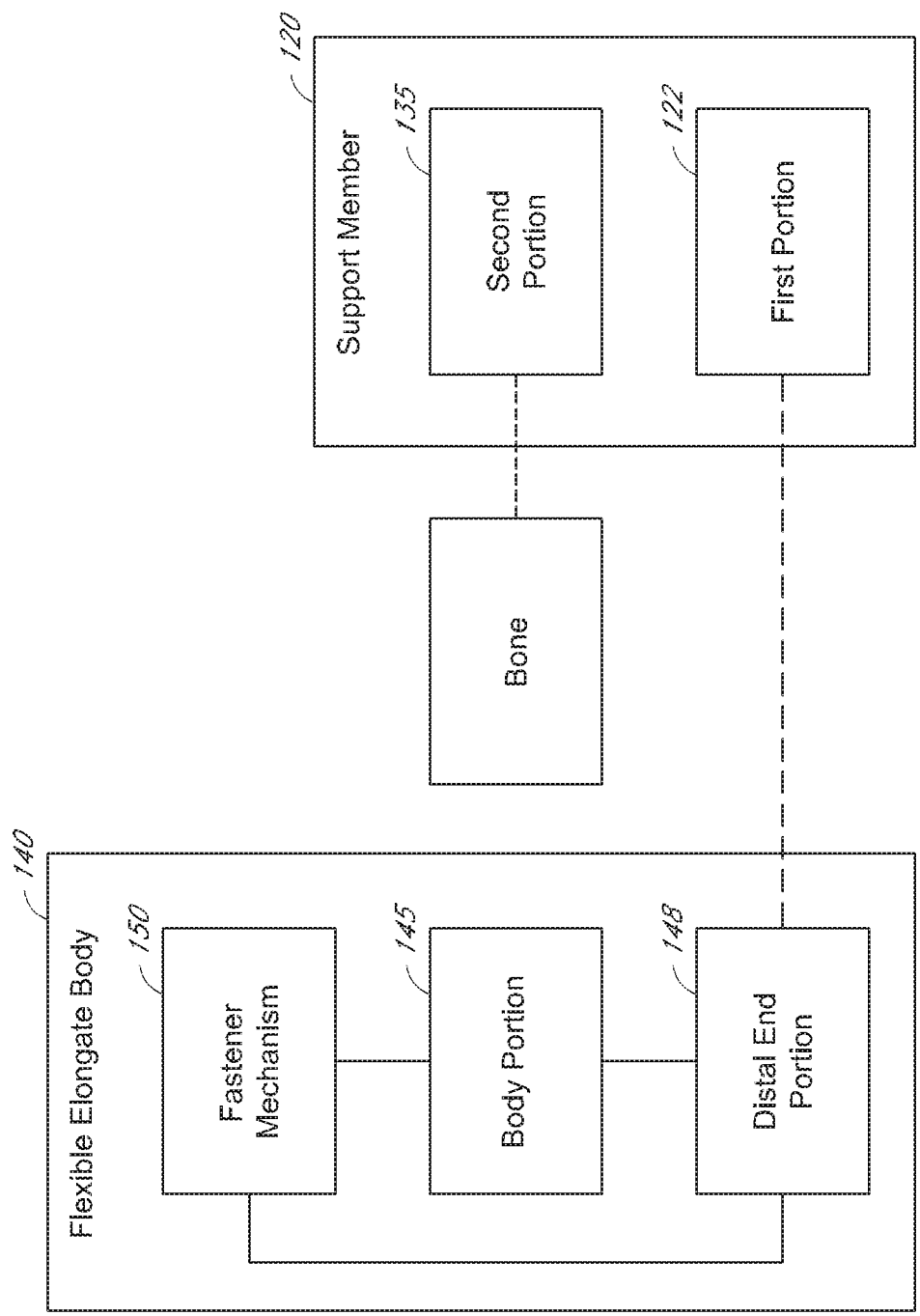
FIG. 7 is a block diagram of a bone stabilization and distraction apparatus according to an embodiment.

FIG. 7 is a schematic block diagram of a flexible elongate body 140 (also referred to herein as "flexible band" or simply "band") and a support member 120, according to an embodiment. The band 140 includes at least a body portion 145, a distal end portion 148, and an attachment connection 150 (alternatively referred to herein as "fastener mechanism"). The band 140 can be formed from any suitable biocompatible material such as, for example, stainless steel, titanium, polyether ether ketone (PEEK), nylon, or the like. Moreover, the band 140 can be any suitable shape, size, or configuration. In some embodiments, the size or shape of the band 140 can be associated with an intended usage. For example, in some embodiments, a first band can be intended to stabilize and/or fixate one or more cervical vertebra and a second band can be intended to stabilize and/or fixate one or more lumbar vertebra. In this manner, the first band can have a first size that is substantially smaller than a second size of the second band. In other embodiments, the size and shape need not be associated with an intended usage.

The fastener mechanism 150 is configured to accept at least a portion of distal end portion 148 and/or the body portion 145, as further described herein. The fastener mechanism 150 is disposed at a proximal end of the band 140. In some embodiments, the fastener mechanism 150 defines a lumen (not shown in FIG. 7) configured to accept at least a portion of distal end portion 148 and/or the body portion 145. In some embodiments, the lumen of fastener mechanism 150 can have a cross-sectional area that is significantly smaller than a cross-sectional area of at least a portion of the body portion 145. In this manner, the portion of the body portion 145 can be prevented from advancing through fastener mechanism 150. In some embodiments, the fastener mechanism 150 can include a ratchet (not shown in FIG. 7) configured to engage a surface of the distal end portion 148 and/or the body portion 145. In this manner, the fastener mechanism 150 can be configured to allow the distal end portion 148 and/or the body portion 145 to advance through fastener mechanism 150 in a first direction and substantially limit the movement of the distal end portion 148 and/or the body portion 145 in a second direction, opposite the first direction.

The body portion 145 is an elongate that extends from a portion of the fastener mechanism 150. More specifically, the body portion 145 of the band 140 can be monolithically (or unitarily) formed with the fastener mechanism 150 such that the body portion 145 is an linear portion between the fastener mechanism 150 and the distal end portion 148. In other embodiments, the body portion 145 can be formed separately from and coupled to the fastener mechanism 150 in any suitable manner (e.g., coupled via an adhesive, a weld, a friction fit, a threaded fit, or the like). The body portion 145 can be any suitable configuration. For example, in some embodiments, the body portion 145 can have a cross-sectional shape that is polygonal (e.g., square, rectangular, trapezoidal, etc.) or oval (e.g., circular, elliptical, oblong, etc.). In some embodiments, the cross-sectional shape of the body portion 145 can be associated with one or more characteristics of the bone or bone portion against which the body portion 145 may contact. For example, while the body portion 145 can have a substantially square cross-sectional shape, a set of edges of the body portion 145 can be rounded, partially rounded, and/or otherwise shaped to compliment the shape of a bone or bone portion, and/or to reduce digging or grinding into the bone or bone portion. In this manner, use of band 140 can cause little or no damage to the bone or bone portions contacted by band 140.

In some embodiments, the body portion 145 can define a substantially uniform cross-sectional area along a longitudinal axis (e.g., a centerline) of the band 140. In other embodiments, the cross-sectional area of the body portion 145 can vary along the longitudinal axis (centerline) of the band 140. For example, in some embodiments, the body portion 145 can have a cross-sectional area that is substantially tapered (i.e., reduced) from a proximal end (e.g., adjacent the fastener mechanism 150) to a distal end (e.g., adjacent the distal end portion 148). In some embodiments, the cross-sectional area of the body portion 145 can be associated with or complimentarily fit with the cross-sectional area of the lumen defined by the fastener mechanism 150 (the attachment connection 150 described above). In this manner, at least a portion of the body portion 145 can have a cross-sectional area that is sufficiently small such that the body portion 145 can be at least partially disposed within the lumen of the fastener mechanism 150.

The body portion 145 can be configured to include a gear rack (not shown in FIG. 7) configured to engage the ratchet (not shown in FIG. 7) of the fastener mechanism 150. As described above, the gear rack can be configured to engage the ratchet of the fastening member 150 such that the ratchet allows the body portion 145 to travel through the fastener mechanism 150 in the first direction and substantially limits the movement of the body portion in the second direction, opposite the first direction. In some embodiments, the gear rack can be configured to include a set of individual gears that extend from a surface of the body portion 145. In other embodiments, the body portion 145 can define the set of individual gears (e.g., the gears each include a top surface that is disposed at or below a surface of the body portion 145). The gears included in the set of gears can be any suitable shape, size, or configuration. For example, in some embodiments, the gears are substantially cubed. In other embodiments, the gears can be triangular such that the gears form, for example, teeth. In this manner, the gears included in the gear rack can be configured to engage the ratchet of the fastener mechanism 150, as described above.

The distal end portion 148 is configured to extend from the body portion 145 of the band 140. More specifically, the distal end portion 148 is disposed adjacent the distal end of the body portion 145 such that the body portion 145 is disposed between the distal end portion 148 and the fastener portion 150. In some embodiments, the distal end portion 148 can have a cross-sectional area that is substantially similar to the cross-sectional area of the body portion 145. In other embodiments, the distal end portion 148 can have a cross-sectional area that is substantially smaller than the cross-sectional area of the body portion 145. In such embodiments, the distal end portion 148 and the body portion 145 can collectively define a discontinuity defining a stepwise reduction in the cross-sectional area. In other embodiments, the body portion 145 and/or the distal end portion 148 can define a tapered portion such that the band 140 is tapered between smaller cross-sectional area of the distal end portion 148 and the larger cross-sectional area of the body portion 145.

While not shown in FIG. 7, in some embodiments, the distal end portion 148 can include a gear rack that is substantially similar to the gear rack of the body portion 145. In this manner, the gear rack can extend substantially continuously across a portion of the distal end portion 148 and a portion of the body portion 145. In other embodiments, the distal end portion 148 of the band 140 does not include or define a gear rack.

The support member 120 includes a first portion 122 and a second portion 135. The support member 120 can be formed from any suitable biocompatible material such as, for example, stainless steel, titanium, polyether ether ketone (PEEK), nylon, or the like. The first portion 122 can include an aperture (not shown in FIG. 7) that is configured to receive the distal end portion 148 of band 140. In such embodiments, a proximal end portion of the first portion 122 can define the aperture.

The second portion 135 is configured to be coupled to a bone portion. In some embodiments, the second portion 135 can be substantially similar to the first portion 122 and can include an aperture that is configured to receive a distal end portion of a second band 140 (not shown in FIG. 7) that is configured to surround a bone portion. The second portion 135 can include a fixation portion and can be configured to be coupled to a bone portion. In such embodiments, the fixation portion of the second portion 135 can include a screw, such as for example, a bone screw.

In some embodiments, the support member 120 can includes a third portion (not shown in FIG. 7) configured to couple the first portion 122 to the second portion 135. In such embodiments, a distal end portion of the first portion 122 can define a coupler portion configured to secure the first portion 122 to the third portion. In such embodiments, the coupler portion can include a threaded portion and a screw portion. In some embodiments, the second portion 135 can be coupled directly to the first portion 122 (see, e.g., FIG. 12A).

In use, the band 140 and the support member 120 can stabilize a first vertebra and/or a second vertebra, and/or can be configured to define a distraction between the first vertebra and the second vertebra. In some uses, the band 140 and the support member 120 can stabilize the first vertebra to a second vertebra by securing an articular process of the first vertebra to an articular process of a second vertebra by securing a facet of the articular process of the first vertebra with a facet of the articular process of the second vertebra (see, e.g., FIG. 10A). In some other uses, the band 140 and the support member 120 can stabilize the first vertebra to a second vertebra by securing an articular process of the first vertebra to a transverse process of a second vertebra by securing a facet of the articular process of the first vertebra with a facet of the transverse process of the second vertebra (see, e.g., FIGS. 11A and 13A). In yet some other uses, the band 140 and the support member 120 can stabilize the first vertebra to a second vertebra by securing an articular process of the first vertebra to at least one of an articular process of the second vertebra, a transverse process of the first vertebra, or to a transverse process of a second vertebra by securing a facet of the articular process of the first vertebra to at least one of a facet of the articular process of the second vertebra, a facet of the transverse process of the first vertebra, or a facet of the transverse process of the second vertebra (see, e.g., FIG. 12A). In some other uses, the band 140 and the support member 120 can stabilize the first vertebra to a second vertebra by securing a transverse process of the first vertebra to a transverse process of a second vertebra by securing a facet of the transverse process of the first vertebra with a facet of the transverse process of the second vertebra (see, e.g., FIGS. 14A and 15A).

For example, the band 140 can be placed into a suitable position relative to the first vertebra and/or the second vertebra, and the distal end portion 148 of the band can be inserted into the lumen of the fastener member 150 such that the body portion 145 substantially encircles at least a portion of the first vertebra and/or the second vertebra. Similarly stated, the distal end portion 148 can be inserted in to the lumen of the fastener mechanism 150 such that the band 140 forms a loop about a process of the first vertebra and/or a process of the second vertebra. In this manner, the distal end portion 148 and/or the body portion 145 can be advanced through the lumen of the fastener mechanism 150 such that the volume disposed within the loop formed by the band 140 is reduced. Thus, the band 140 exerts a compressive force on the articular process of the first vertebra and the articular process of the second process.

In some instances, with the band 140 at least partially tightened and/or fully tightened, a fixation portion of the second portion 135 of the support member 120 can be fixed to a bone portion, for example a transverse process of a vertebra. In some instances, fixing the second portion 135 to a bone portion can include advancing a fastener, for example a screw, through the fixation portion and into the bone portion. In some instances, with the band 140 at least partially tightened and/or fully tightened, a distal end portion of a second band (not shown in FIG. 7) can be disposed through an aperture (not shown in FIG. 7) of the second portion 135 of the support member 120, and the distal end portion of the second band can be a secured to a bone portion as described above with reference to band 140.

In some embodiments, a third portion (not shown in FIG. 7) of the support member 120 can be disposed between the first portion 122 and the second portion 135. In such embodiments, the first portion 122 can be coupled to the third portion at a first point along a length of the third portion, and the second portion 135 can be coupled to the third portion at a second point along the length of the third portion. The first point and the second point can be spaced apart to define a distraction between the first portion 122 and the second portion 135 to define a corresponding distraction between a first vertebra and a second vertebra. In this manner, the distance between the first point and the second point, e.g., the distance between the first portion 122 and the second portion 135, can be increased (or decreased) to increase (or decrease) the distraction between the first vertebra and the second vertebra.

Figure 8A:
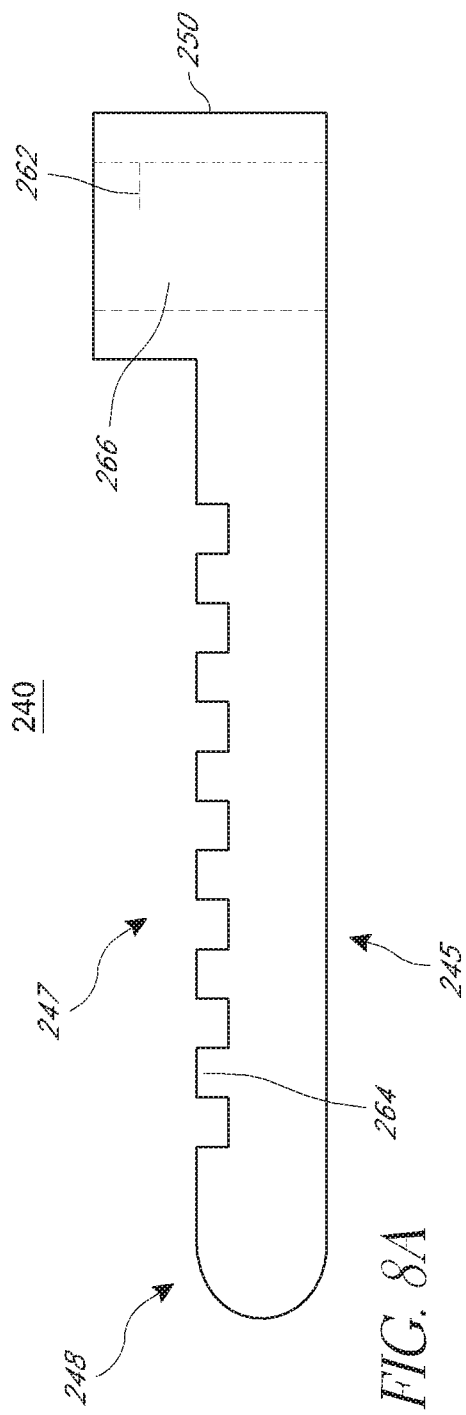
FIGS. 8A and 8B are schematic illustrations of a flexible elongate body according to an embodiment.
Figure 8B:
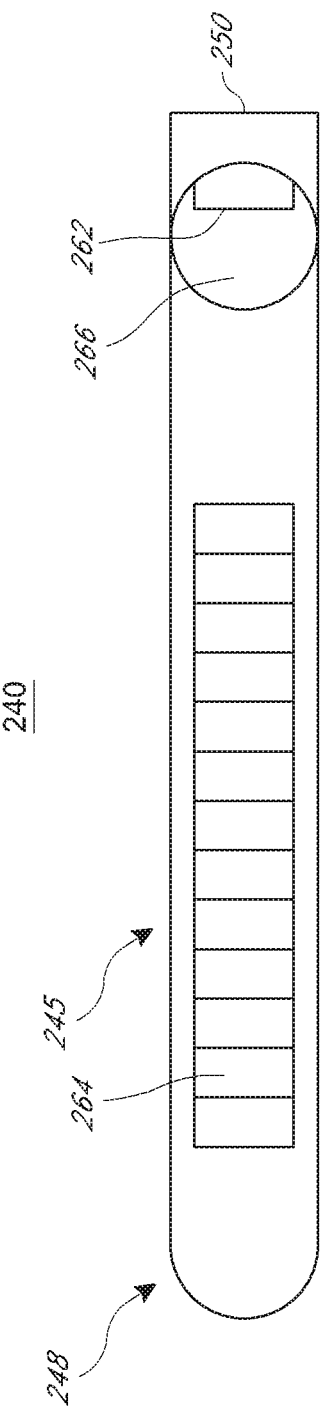

FIG. 8A is a side view and FIG. 8B is a top view of a flexible elongate body 240 (also referred to herein as "band") according to an embodiment. The band 240 can be similar to the band 140 described above and can include similar components. For example, the band 240 includes an attachment connection 250 (also referred to herein as "fastener mechanism") including a ratchet 262, a body portion 245 including a gear rack 247, and a distal end portion 248. Accordingly, components of the band 240 that are similar to corresponding components of the band 140 described above with reference to FIG. 7 are not described in further detail herein.

As shown in FIG. 8A, each gear 264 included in the gear rack 247 includes a cross sectional area that is rectangular in shape. Said another way, each gear 264 can be a rectangular protrusion configured to extend from a surface of the band 240 (e.g., the body portion and/or the distal end portion 248). The gear rack 247 is configured to engage the ratchet 262 of the fastener mechanism 250, as further described herein. The fastener mechanism 250 defines a lumen 266. The lumen 266 can be any suitable shape, size, or configuration. For example, as shown in FIG. 8B the lumen 266 can have a substantially circular cross-sectional area. The ratchet 262 extends from an inner surface of the fastener member 250 such that the ratchet 262 substantially reduces the size (e.g., the perimeter, circumference, and/or cross-sectional area) of the lumen 266. In this manner, the ratchet 266 can engage the gear rack 247. More specifically, as described in detail with reference to FIG. 7, the distal end portion 248 can be inserted into the lumen 266 of the fastener mechanism 250 and advanced in a first direction such that the gear rack 247 of the distal end portion 248 engages the ratchet 262. In some embodiments, the distal end portion 248 can be advanced through the lumen 266 a sufficient distance such that a portion of the body portion 245 is disposed within the lumen 266. In such embodiments, a portion of the gear rack 247 disposed on (e.g., included in or defined by) the body portion 245 can engage the ratchet 262. In this manner, the arrangement of the ratchet 262 and the gear rack 247 can be such that the distal end portion 248 can be moved in the first direction, thereby tightening the band 240, and the distal end portion 248 can be prevented from moving in a second direction, opposite the first direction, thereby preventing the band 240 from loosening.

The band 240 can be used in any suitable procedure to stabilize and/or fixate a first bone portion to a second bone portion. For example, in some embodiments, the band 240 can be disposed about an articular process of a first vertebra and/or an articular process of a second vertebra. In this manner, the distal end portion 248 and/or the body portion 245 can be positioned within the lumen 266 of the fastener mechanism 250 such that the band 240 forms a loop of suitable tightness about the first vertebra and/or the second vertebra. The band 240 can be used in conjunction with any suitable support member configured to facilitate the stabilization, fixation and/or distraction of the first vertebra to the second vertebra.

In some embodiments, the band 240 can be used in any procedure described in or similar to those in U.S. patent application Ser. No. 12/859,009; filed Aug. 18, 2010, and titled "Vertebral Facet Joint Drill and Method of Use" (referred to as "the '009 application"), the disclosure of which is incorporated herein by reference in its entirety. In some embodiments, the band 240 can be used in conjunction with a spacer such as those described in the '009 application. For example, the spacer can be implanted and deployed to restore the space between facets of a superior articular process of a first vertebra and an inferior articular process of an adjacent vertebra. The spacer can be implanted and deployed to help stabilize adjacent vertebrae with adhesives and/or to deliver a medication. For example, in some embodiments, the spacer can be at least temporarily maintained in a desired position via an adhesive while the band 240 is positioned relative to the first vertebra and/or second vertebra. In some embodiments, an adhesive can be used in conjunction with the band 240 to stabilize and/or fixate the first vertebra to the second vertebra.

In some embodiments, the spacer can be, for example, substantially disc shaped. In other embodiments, the spacer can be other shapes, e.g., square, elliptical, or any other shape. The spacer can include a first side and a second side. The first side and/or the second side can be, for example, convex, concave, or flat. Said another way, the first side of the spacer can be concave, convex, or flat, and the second side of the spacer can be concave, convex, or flat, for example, the first side can be concave and the second side concave, the first side can be concave and the second side convex, etc. The spacer can include the same materials as band 140. In some embodiments, the spacer can include substances configured to release medication and/or increase the stability of a vertebra and/or band 140. As discussed above, the substances can include a medicine(s) and/or an adhesive(s).

Figure 9A:
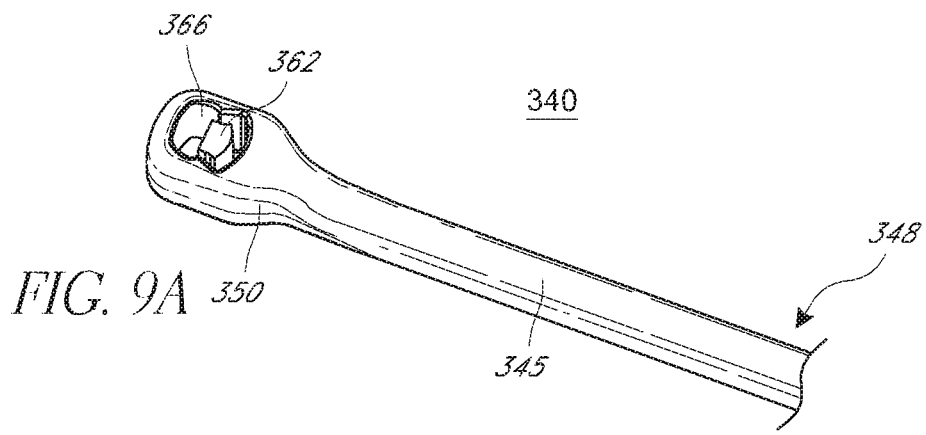
FIGS. 9A-9C are various views of a flexible elongate body according to another embodiment.
Figure 9B:
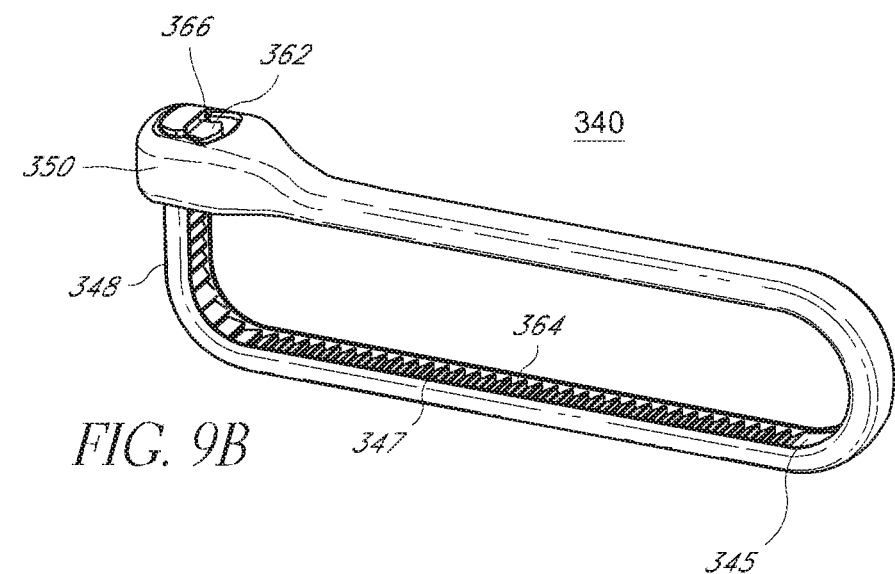
Figure 9C:
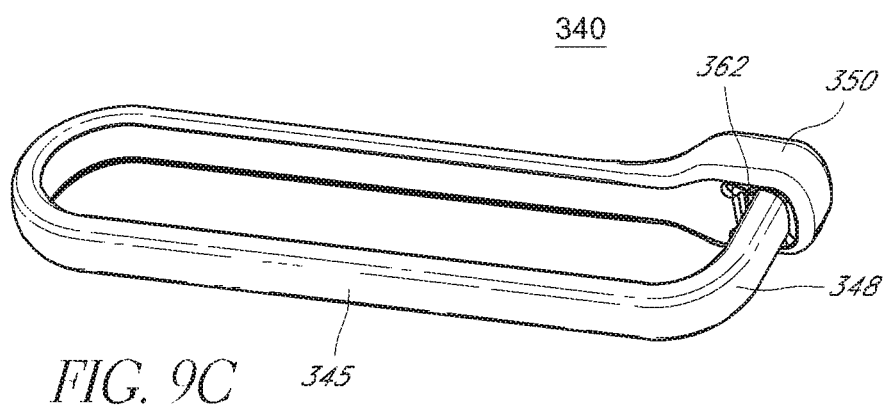

FIGS. 9A-9C illustrate a flexible elongate body 340 (also referred to herein as "band") according to an embodiment. The band 340 can be similar to band 140 described above with reference to FIG. 7 and can include similar components. By way of example, band 340 includes a fastener mechanism 350, a body portion 345, and a distal end portion 348. As shown in FIGS. 9A-9C, the band 340 can be monolithically (or unitarily) constructed in an elongate shape and can have a substantially rectangular cross-sectional shape. More specifically, the band 340 can have a substantially rectangular shape including rounded edges configured to reduce digging or grinding into the bone or portion thereof. The fastener mechanism 350 defines a lumen 366 and includes ratchet 362. The body portion 345 includes a gear rack 347 having a set of gears 364. In this manner, the distal end portion 348 can be inserted into the lumen 366 of the fastener member 350 such that the gear rack 347 engages the ratchet 362, as described in detail above.

Figure 10A:
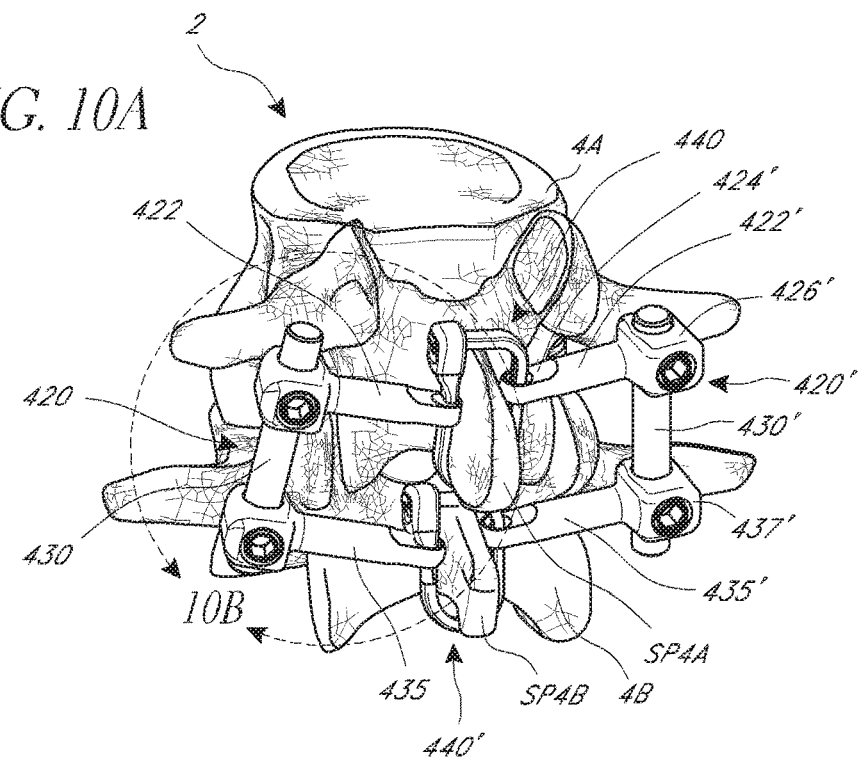
FIG. 10A is a posterior perspective view of a portion of the vertebral column depicting a stabilized vertebra including bone stabilization and distraction apparatus according to an embodiment.
Figure 10B:
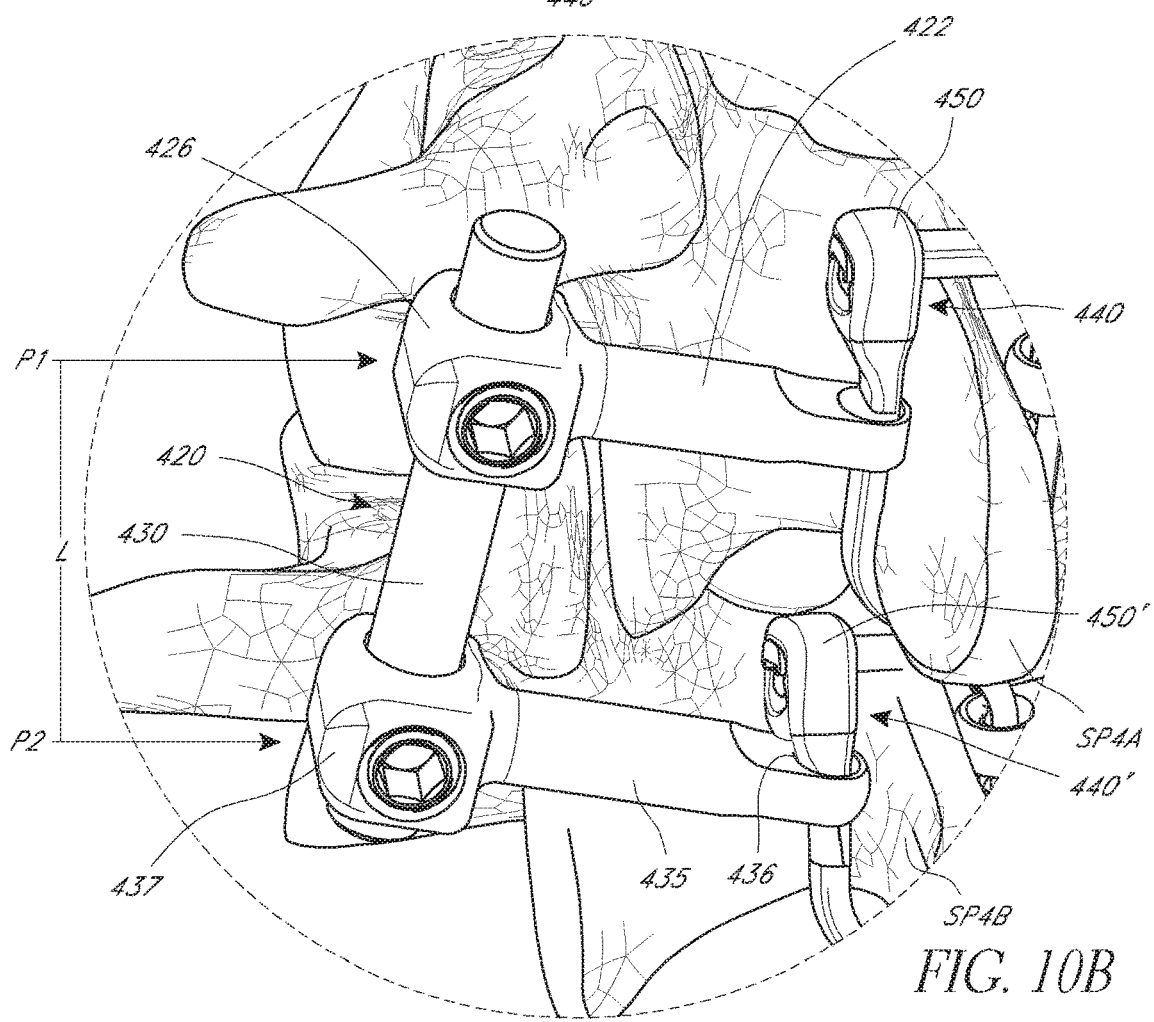
FIG. 10B is an enlarged view of a portion of the vertebral column of FIG. 10A identified as region $X_1$.

FIGS. 10A and 10B depict a bone stabilization and distraction apparatus, specifically a band 440, a band 440', a support member 420, and a support member 420' stabilizing a vertebra 4A of spinal column 2 with a vertebra 4B of spinal column 2, and defining a distraction between vertebra 4A and vertebra 4B. The bands 440, 440' can be similar to the band 140 described above and can include similar components. For example, the band 440 includes an attachment connection 450 (also referred to herein as "fastener mechanism"). Support members 420, 420' can be similar to the support member 120 described above and can include similar components.

As shown in FIGS. 10A and 10B, the band 440 can be used to stabilize a first vertebra 4A and a second vertebra 4B, and to define a distraction between the first vertebra 4A and a second vertebra 4B, via the spinous articular process SP4A (also referred to herein as "process SP4A") of the first vertebra 4A and the spinous articular process SP4B (also referred to herein as "process SP4B") of the second vertebra 4B. Specifically, a distal end portion (not shown) of the band 440 can be inserted into an aperture 424 of a first portion 422 of a support member 420, and the distal end portion of the band 440 can be inserted into the aperture 424' of a first portion 422' of a support member 420'. The fastener mechanism 450 can receive the distal end portion of the band 440 such that the body portion 445 forms a loop that substantially encircles the process SP4A of the first vertebra 4A. Similarly, a distal end portion (not shown) of the band 440' can be inserted into an aperture 436 of a second portion 435 of the first support member 420 and the distal end portion of the band 440' can be inserted into the aperture 436' of the second portion 435' of the support member 420'. The fastener mechanism 450' can receive the distal end portion (not shown) of the band 440' such that the body portion 445' forms a loop that substantially encircles the process SP4B of the second vertebra 4B, (as described in detail above).

A third portion 430 of first support member 420 can be disposed between first portion 422 and second portion 435. The third portion 430 can be coupled to a coupler portion 426 of first portion 420 at point P1 and can be coupled to a coupler portion 437 of second portion 435 at P2. Similarly a third portion 430' of support member 420' can be disposed between first portion 422' and second portion 435'. The third portion 430' can be coupled to a coupler portion 426' of first portion 422' at point P1' (not labeled in FIG. 10A) and can be coupled to a coupler portion 437' of second portion 435' at point P2' (not labeled in FIG. 10A). A length L1 between point P1 and point P2, along with a length L1' between point P1' and point P2', can define a distraction between vertebra 4A and vertebra 4B.

For example, support member 420 and support member 420' are rigid structures that maintain a distraction by pushing on band 440 and band 440', which are fixedly coupled to process SP4A and process SP4B. Specifically, first portion 422 and first portion 422' can push, in a first direction, on band 440, which is fixedly coupled to process SP4A. Similarly, second portion 435 and second portion 435' can push, in a second direction opposite the first direction, on band 440', which is fixedly coupled to process SP4B.

Figure 11A:
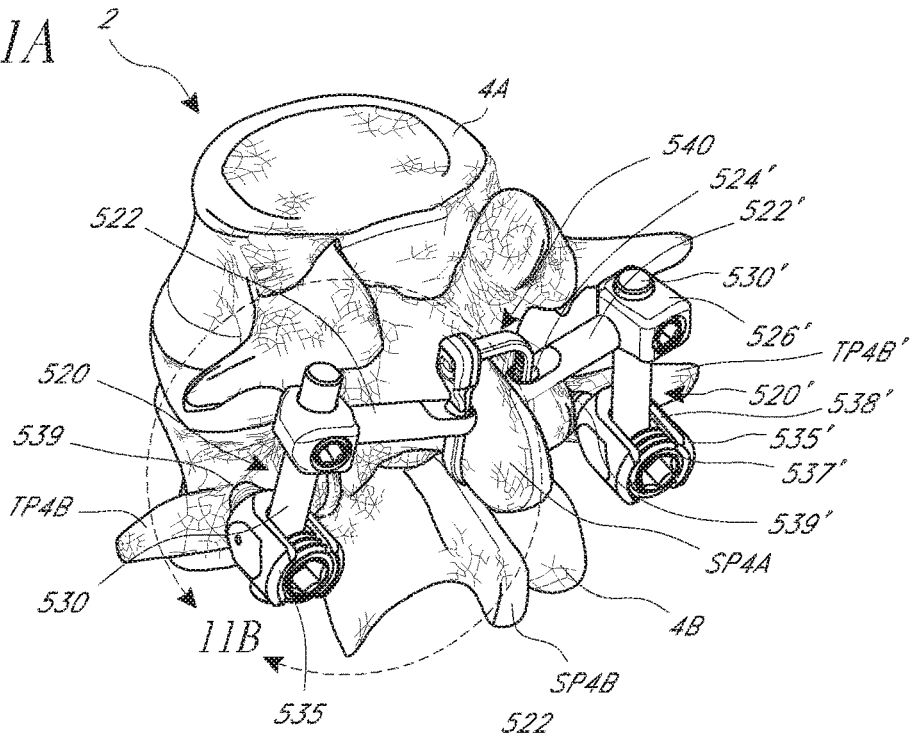
FIG. 11A is a posterior view of the portion of the vertebral column depicting a stabilized vertebra including a bone stabilization and distraction apparatus according to an embodiment.
Figure 11B:
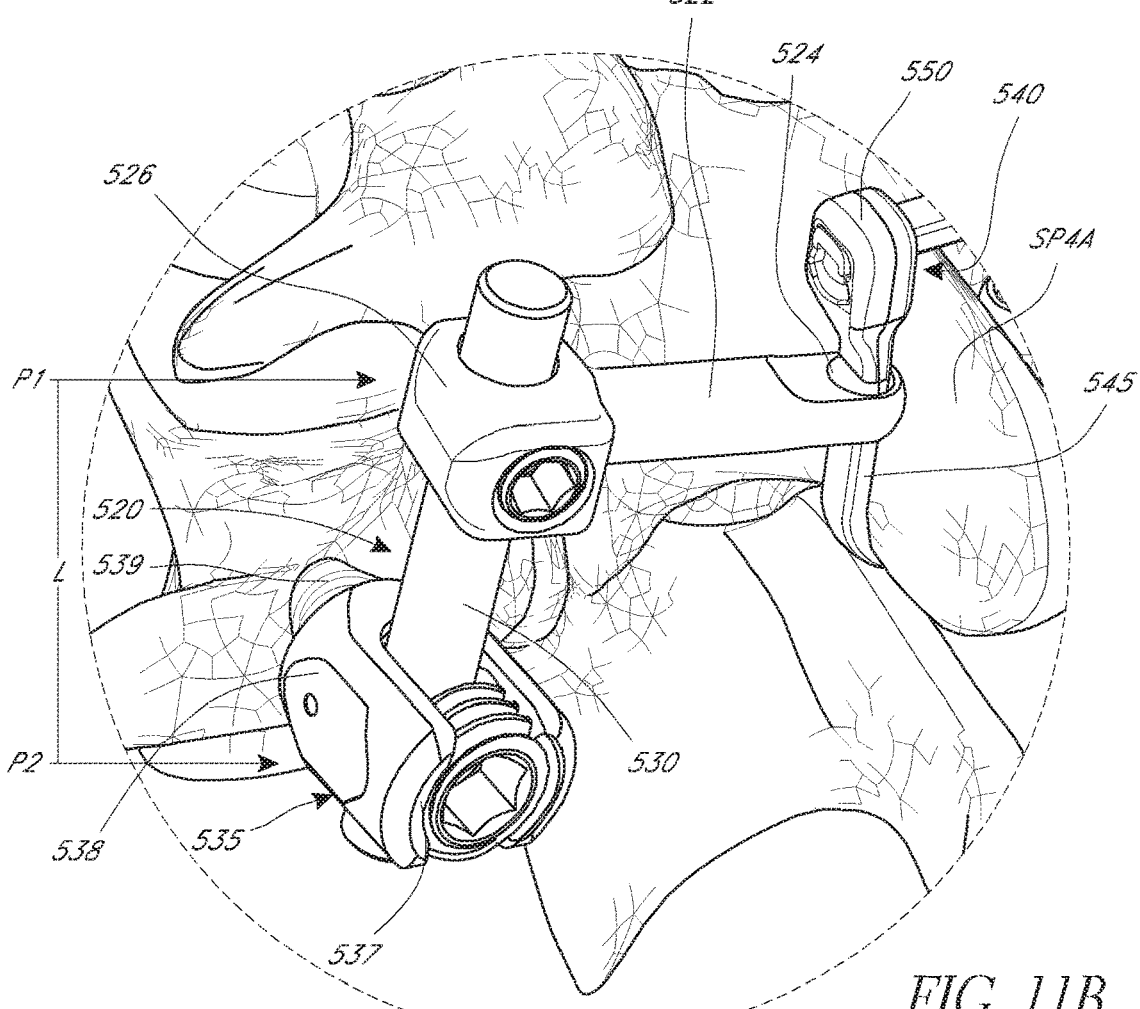
FIG. 11B is an enlarged view of a portion of the vertebral column of FIG. 11A identified as region $X_2$.

FIGS. 11A and 11B depict a bone stabilization and distraction apparatus, specifically a band 540, a support member 520, and a support member 520' stabilizing a vertebra 4A of spinal column 2 with a vertebra 4B of spinal column 2, and defining a distraction between vertebra 4A and vertebra 4B. The band 540 can be similar to the band 140 described above and can include similar components, and support members 520, 520' can be similar to the support member 120 described above and can include similar components. For example, the band 540 includes an attachment connection 550 (also referred to herein as "fastener mechanism").

As shown in FIGS. 11A and 11B, the band 540, the support member 520 and the support member 520' can be used to stabilize a first vertebra 4A and a second vertebra 4B, and to define a distraction between the first vertebra 4A and a second vertebra 4B, via the spinous articular process SP4A (also referred to herein as "process SP4A") of the first vertebra 4A and the transverse articular process SP4B (also referred to herein as "process SP4B") of the second vertebra 4B. Specifically, a distal end portion (not shown) of the band 540 can be inserted into an aperture 524 of a first portion 522 of the support member 520, and the distal end portion of the band 540 can be inserted into the aperture 524' of the first portion 522' of the support member 520'. The fastener mechanism 550 can receive the distal end portion of the band 540 such that the body portion 545 forms a loop that substantially encircles the process SP4A of the first vertebra 4A. A fastener 539 can be advanced through a fixation portion 538 of second portion 535 of support member 520 and into transverse process TP4B. A fastener 539' can be advanced through a fixation portion 538' of second portion 535' of support member 520' and into transverse process TP4B'.

A third portion 530 of support member 520 can be disposed between first portion 520 and second portion 535. The third portion 530 can be coupled to a coupler portion 526 of first portion 520 at point P1 and can be coupled to a coupler portion 537 of second portion 535 at P2. Similarly a third portion 530' of support member 520' can be disposed between first portion 520' and second portion 535'. The third portion 530' can be coupled to a coupler portion 526' of first portion 520' at point P1' (not labeled in FIG. 10A) and can be coupled to a coupler portion 537' of second portion 535' at point P2' (not labeled in FIG. 10A). A length L between point P1 and point P2, along with a length L' (not labeled in FIG. 10A) between point P1' and point P2', can define a distraction between vertebra 4A and vertebra 4B.

For example, support member 520 and support member 520' are rigid structures that maintain a distraction by pushing on band 540 which is fixedly coupled to SP4A and processes TP4B, TP4B'. Specifically, first portion 522 and first portion 522' can push, in a first direction, on band 540, which is fixedly coupled to process SP4A. Similarly, second portion 535 and second portion 535' can push, in a second direction opposite the first direction, on process TP4B and process TP4B', respectively.

Figure 12A:
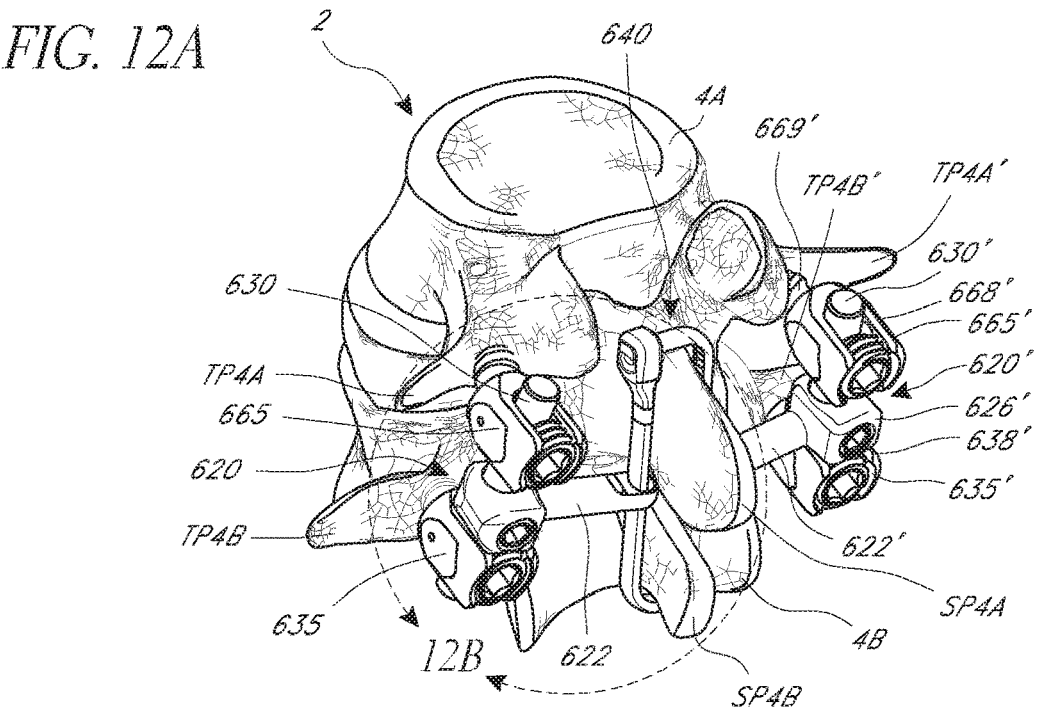
FIG. 12A is a posterior view of the portion of the vertebral column depicting a stabilized vertebra including a bone stabilization and distraction apparatus according to an embodiment.
Figure 12B:
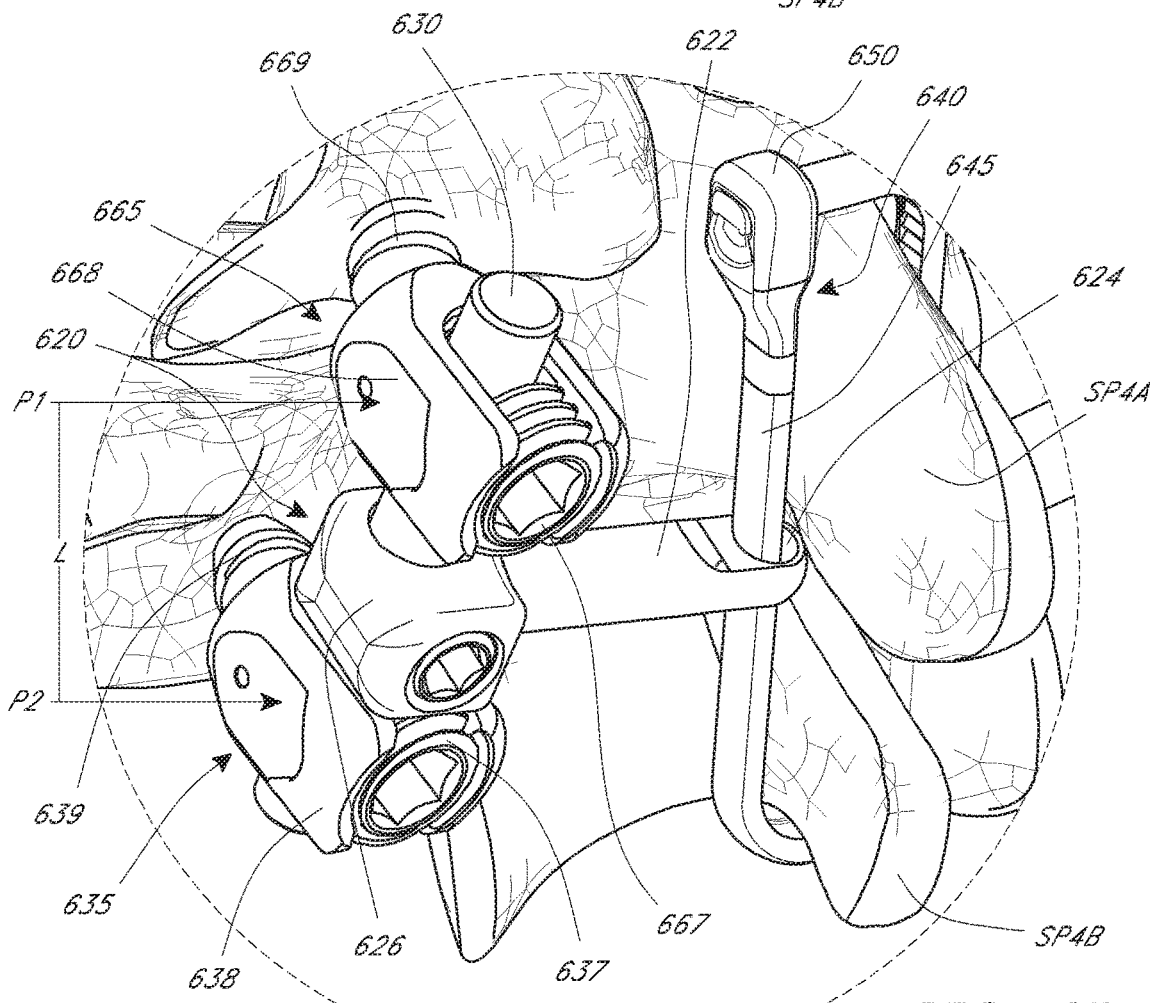
FIG. 12B is an enlarged view of a portion of the vertebral column of FIG. 12A identified as region $X_3$.

FIGS. 12A and 12B depict a bone stabilization and distraction apparatus, specifically a band 640, a support member 620, and a support member 620' stabilizing a vertebra 4A of spinal column 2 with a vertebra 4B of spinal column 2, and defining a distraction between vertebra 4A and vertebra 4B. The band 640 can be similar to the band 140 described above and can include similar components, and support members 620, 620' can be similar to the support member 120 described above and can include similar components. For example, the band 640 includes an attachment connection 650 (also referred to herein as "fastener mechanism"). As seen in FIGS. 12A and 12B, unlike support member 520 of FIGS. 11A and 11B, which includes a first portion 522, a second portion 535 and a third portion 530, the support member 620 includes a first portion 622, a second portion 635, a third portion 630, and a fourth portion 665. The fourth portion 665 can be similar to the second portion 635.

As shown in FIGS. 12A and 12B, the band 640, the support member 620, and the support member 620' can be used to stabilize a first vertebra 4A and a second vertebra 4B, and to define a distraction between the first vertebra 4A and a second vertebra 4B, via the spinous articular process SP4A (also referred to herein as "process SP4A") of the first vertebra 4A and the transverse articular processes TP4A, TP4A' (also referred to herein as "process TP4A" and "process TP4A'") of the first vertebra 4A, and via the spinous articular process SP4B (also referred to herein as "process SP4B") of the second vertebra 4B and the transverse articular processes TP4B, TP4B' (also referred to herein as "process TP4B" and "process TP4B'") of the second vertebra 4B. Specifically, a distal end portion (not shown) of the band 640 can be inserted into an aperture 624 of a first portion 622 of the support member 620, and the distal end portion of the band 640 can be inserted into the aperture (not shown in FIG. 12A) of the first portion 622' of the support member 620'. The fastener mechanism 650 can receive the distal end portion of the band 640 such that the body portion 645 forms a loop that substantially encircles the process SP4A and process SP4B. A fastener 639 can be advanced through a fixation portion 638 of second portion 635 of support member 620 and into transverse process TP4B. A fastener 669 can be advanced through a fixation portion 668 of fourth portion 665 of support member 620 and into transverse process TP4A. A fastener (not shown in FIG. 12A) can be advanced through a fixation portion 638' of second portion 635' of support member 620' and into transverse process TP4B'. A fastener 669' can be advanced through a fixation portion 668' of fourth portion 665' of support member 620' and into transverse process TP4A.

A third portion 630 of support member 620 can be disposed through first portion 620 and between second portion 635 and fourth portion 665. The third portion 630 can be coupled to a coupler portion 626 of first portion 620, can be coupled to a coupler portion 637 of second portion 635 at P2, and can be coupled to a coupler portion 667 of fourth portion 665 at P1. Similarly a third portion 630' of support member 620' can be disposed through first portion 620' and between second portion 635' and fourth portion 665'. The third portion 630' can be coupled to a coupler portion 626' of first portion 620', can be coupled to a coupler portion 637' (not shown in FIG. 12A) of second portion 635' at P2' (not shown in FIG. 12A), and can be coupled to a coupler portion 667' (not shown in FIG. 12A) of fourth portion 665 at P1' (not shown in FIG. 12A). A length L1 between point P1 and point P2, along with a length L1' between point P1' and point P2', can define a distraction between vertebra 4A and vertebra 4B.

For example, support member 620 and support member 620' are rigid structures that maintain a distraction by pushing on processes TP4B, TP4B' and processes TP4A, TP4A'. Specifically, fourth portion 665 and fourth portion 665', which are fixedly coupled to second portion 635 and second portion 635', can push, in a first direction, on process TP4A and process TP4A', and second portion 635 and second portion 635' can push, in a second direction opposite the first direction, on process TP4B and process TP4B', respectively.

Figure 13A:
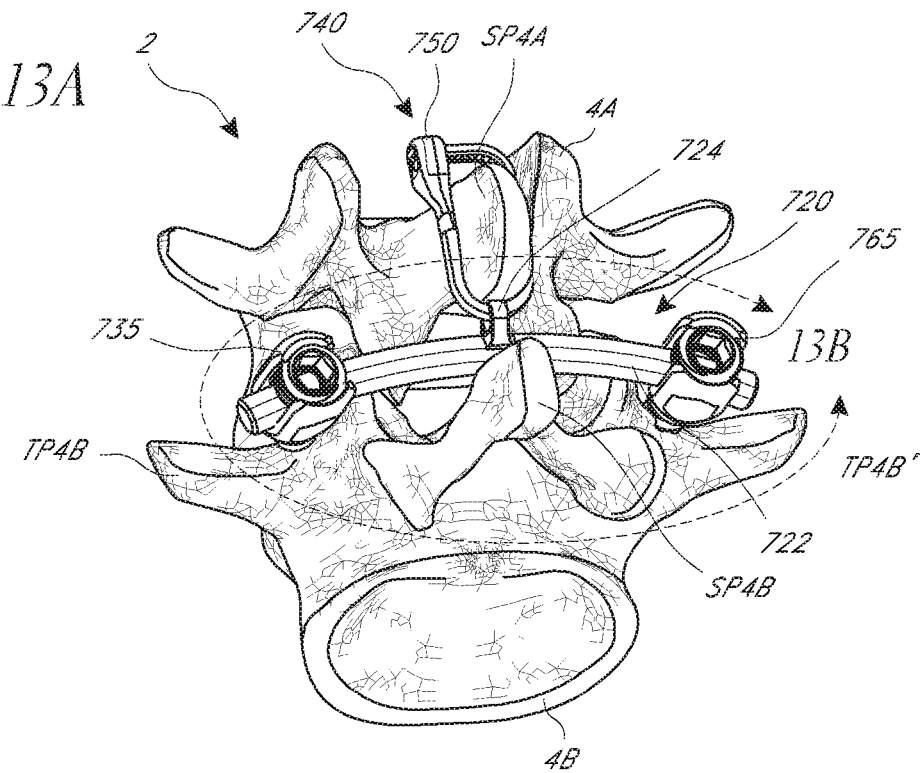
FIG. 13A is a posterior view of the portion of the vertebral column depicting a stabilized vertebra including a bone stabilization and distraction apparatus according to an embodiment.
Figure 13B:
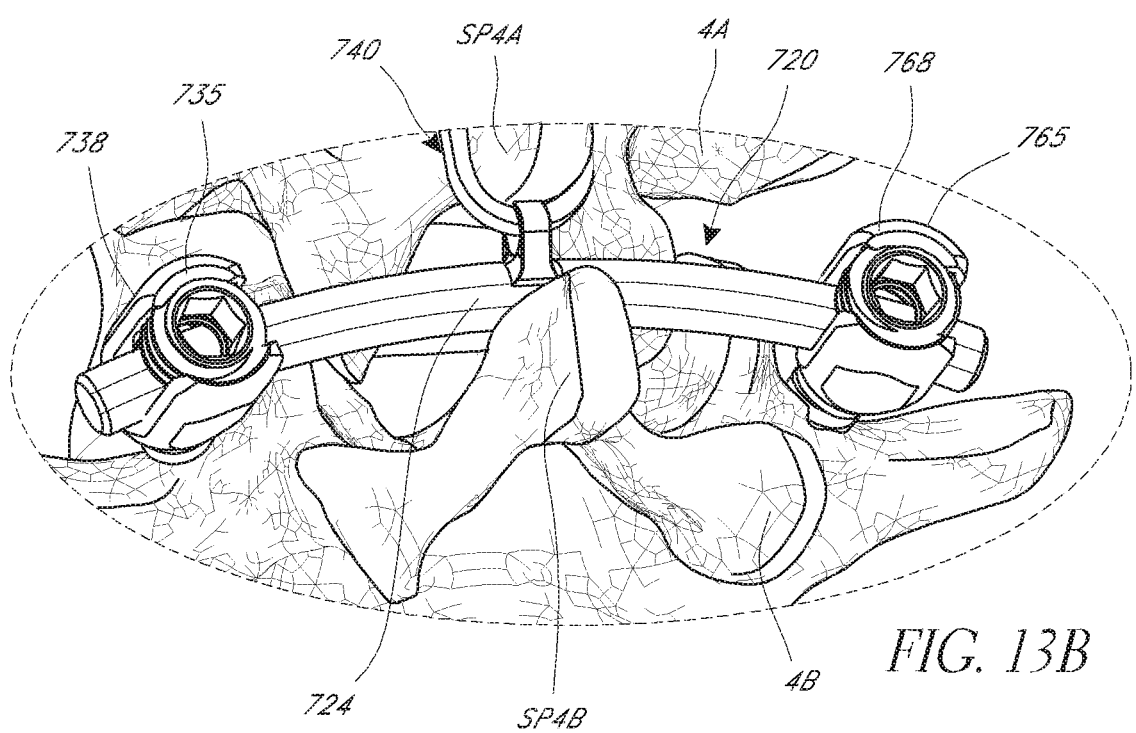
FIG. 13B is an enlarged view of a portion of the vertebral column of FIG. 13A identified as region $X_4$.

FIGS. 13A and 13B depict a bone stabilization and distraction apparatus, specifically a band 740 and a support member 720 stabilizing a vertebra 4A of spinal column 2 with a vertebra 4B of spinal column 2, and defining a distraction between vertebra 4A and vertebra 4B. The band 740 can be similar to the band 140 described above and can include similar components, and support member 720 can be similar to the support member 120 described above and can include similar components. For example, the band 740 includes an attachment connection 750 (also referred to herein as "fastener mechanism").

As shown in FIGS. 13A and 13B, the band 740 and support member 720 can be used to stabilize a first vertebra 4A and a second vertebra 4B, and to define a distraction between the first vertebra 4A and the second vertebra 4B, via the spinous articular process SP4A (also referred to herein as "process SP4A") of the first vertebra 4A and the transverse articular processes TP4B, TP4B' (also referred to herein as "process TP4B" and "process TP4B'") of the second vertebra 4B. Specifically, a distal end portion (not labeled) of the band 740 can be inserted into an aperture 724 of a first portion 722 of the support member 720. The fastener mechanism 750 can receive the distal end portion of the band 740 such that the body portion 745 forms a loop that substantially encircles the process SP4A of the first vertebra 4A. A fastener (not shown in FIG. 13A) can be advanced through a fixation portion 738 of second portion 735 of support member 720 and into transverse process TP4B. A fastener 769 can be advanced through a fixation portion 768 of fourth portion 765 of support member 720 and into transverse process TP4B'. In some embodiments, second portion 735 and/or second portion 735' can be moved along a length of the first portion 722. In this manner, a location on processes TP4A and/or TP4B where second portion 735 and/or second portion 735' are fixed can be adjusted.

For example, support member 720 is a rigid structure that maintains a distraction by pushing on processes TP4B, TP4B'. Specifically, second portion 635 and fourth portion 665' can push, in a first direction, on process TP4B and process TP4B'. Similarly, portion 722 can push, in a second direction opposite the first direction, on process SP4B.

Figure 14A:
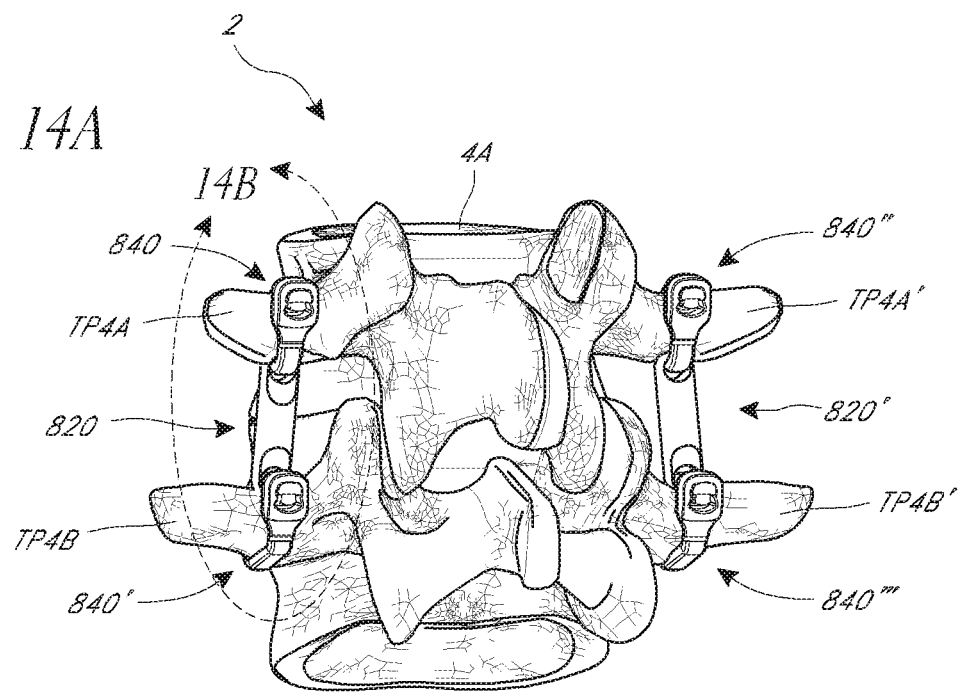
FIG. 14A is a posterior view of the portion of the vertebral column depicting a stabilized vertebra including a bone stabilization and distraction apparatus according to an embodiment.
Figure 14B:
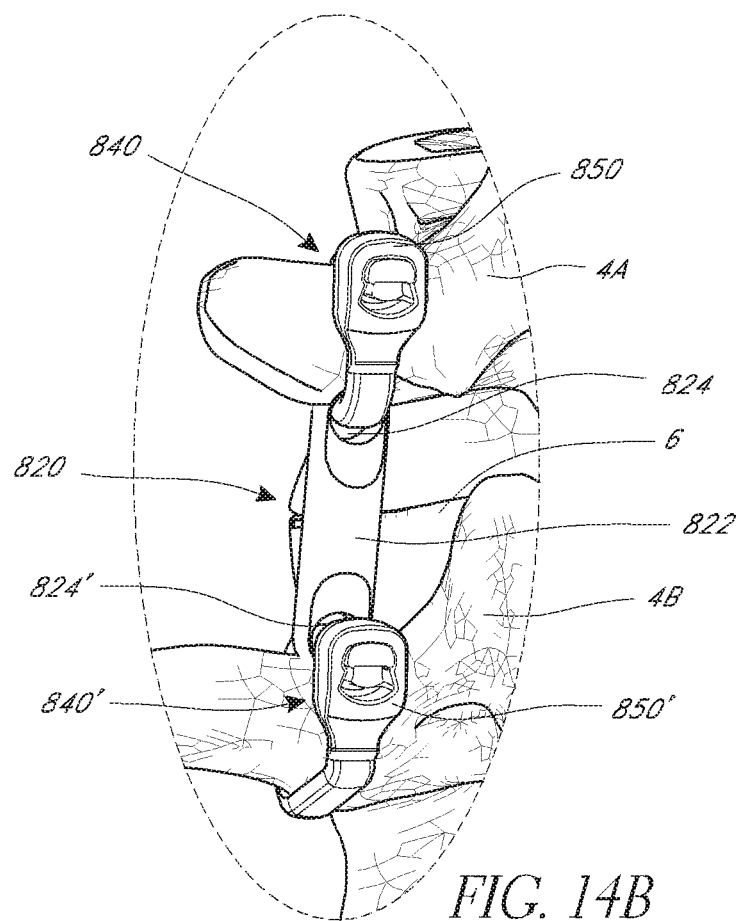
FIG. 14B is an enlarged view of a portion of the vertebral column of FIG. 14A identified as region $X_5$.

FIGS. 14A and 14B depict a bone stabilization and distraction apparatus, specifically a band 840, a band 840', a band 840", a band 840'", a support member 820, and a support member 820' stabilizing a vertebra 4A of spinal column 2 with a vertebra 4B of spinal column 2, and defining a distraction between vertebra 4A and vertebra 4B.

The bands 840, 840', 840", and 840'" can be similar to the band 140 described above and can include similar components, and support members 820, 820' can be similar to the support member 120 described above and can include similar components. For example, the band 840 includes an attachment connection 850 (also referred to herein as "fastener mechanism"). As seen in FIGS. 14A and 14B, unlike support member 520 of FIGS. 11A and 11B, which includes a first portion 522, a second portion 535 and a third portion 530, the support member 820 includes only a first portion 822.

As shown in FIGS. 14A and 14B, the bands 840, 840', 840", and 840'" and the support members 820, 820' can be used to stabilize a first vertebra 4A and a second vertebra 4B, and to define a distraction between the first vertebra 4A and a second vertebra 4B, via the transverse articular processes TP4A, TP4A' (also referred to herein as "process TP4A" and "process TP4A'") of the first vertebra 4A, and via the transverse articular processes TP4B, TP4B' (also referred to herein as "process TP4B" and "process TP4B'") of the second vertebra 4B. Specifically, a distal end portion (not shown) of the band 840 can be inserted into an aperture 824 of a portion 822 of the support member 820, and a distal end portion of the band 840' can be inserted into the aperture 824 of the portion 822 of the support member 820. The fastener mechanism 850 can receive the distal end portion of the band 840 such that the body portion 845 forms a loop that substantially encircles the process TP4A. The fastener mechanism 850' can receive the distal end portion of the band 840' such that the body portion 845' forms a loop that substantially encircles the process TP4B. The process described above with reference to bands 840, 840', support member 820, and processes TP4A, TP4B can be similarly applied to bands 840", 840'", support member 820', and processes TP4A', TP4B'.

As shown in FIGS. 14A and 14B, the distraction between vertebra 4A and vertebra 4B can correspond to a length of the first support member 820 and a length of the support member 820'. While not shown in FIGS. 14A and 14B, the length of one or both of support members 820, 820' can be adjustable (e.g., a single support member can be configured to have a variety of length) or selectable (e.g., a support member can be selected based on its length to provide a particular distraction), and the distraction can be changed depending on an adjusted length of one or both of support members 820, 820' or based on the selected length of one or both of support members 820, 820'.

Figure 15A:
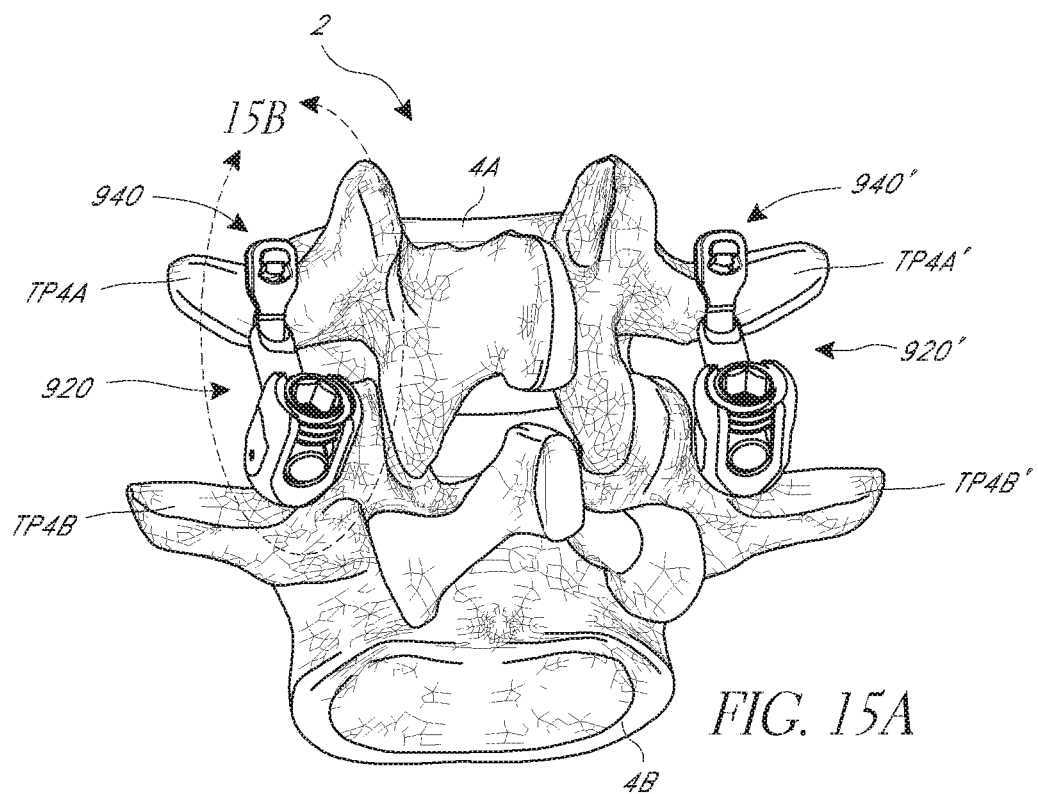
FIG. 15A is a posterior view of the portion of the vertebral column depicting a stabilized vertebra including a bone stabilization and distraction apparatus according to an embodiment.
Figure 15B:
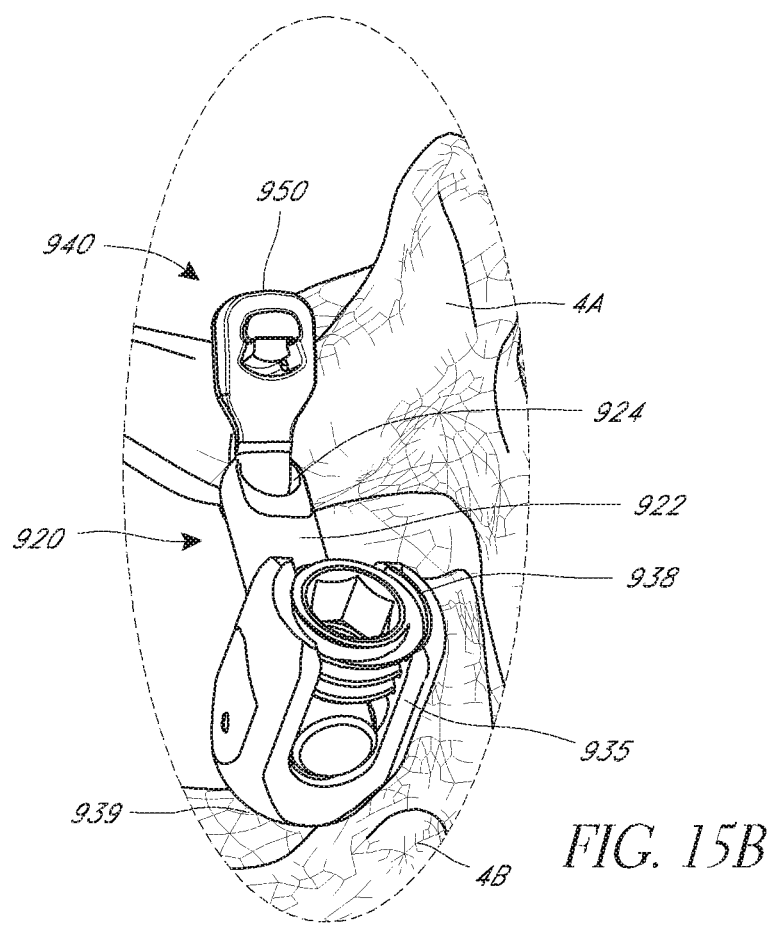
FIG. 15B is an enlarged view of a portion of the vertebral column of FIG. 15A identified as region $X_6$.

FIGS. 15A and 15B depict bone stabilization and distraction apparatus, specifically a band 940, a band 940', a support member 920, and a support member 920' stabilizing a vertebra 4A of spinal column 2 with a vertebra 4B of spinal column 2, and defining a distraction between vertebra 4A and vertebra 4B. The bands 940, 940' can be similar to the band 140 described above and can include similar components, and support members 920, 920' can be similar to the support member 120 described above and can include similar components. For example, the band 940 includes an attachment connection 950 (also referred to herein as "fastener mechanism"). As seen in FIGS. 15A and 15B, unlike support member 520 of FIGS. 11A and 11B, which includes a first portion 522 coupled to a second portion 535 via a third portion 530, the support member 920 includes a first portion 922 directly coupled to the a second portion 935.

As shown in FIGS. 15A and 15B, the bands 940, 940' and the support members 920, 920' can be used to stabilize a first vertebra 4A and a second vertebra 4B, and to define a distraction between the first vertebra 4A and a second vertebra 4B, via the transverse articular processes TP4A, TP4A' (also referred to herein as "process TP4A" and "process TP4A'") of the first vertebra 4A, and via the transverse articular processes TP4B, TP4B' (also referred to herein as "process TP4B" and "process TP4B'") of the second vertebra 4B. Specifically, a distal end portion (not shown) of the band 940 can be inserted into an aperture 924 of a portion 922 of the support member 920. The fastener mechanism 950 can receive the distal end portion of the band 940 such that the body portion 945 forms a loop that substantially encircles the process TP4A. A fastener 939 can be advanced through a fixation portion 938 of second portion 935 of support member 920 and into transverse process TP4B The process described above with reference to bands 940 and support member 920, and processes TP4A, TP4B can be similarly applied to bands 940' and support member 920', and processes TP4A', TP4B'.

As shown in FIGS. 15A and 15B, the distraction between vertebra 4A and vertebra 4B can correspond to a length of the support member 920 and a length of the support member 920'. While not shown in FIGS. 15A and 15B, the length of one or both of support members 920, 920' can be adjustable (e.g., a single support member can be configured to have a variety of length) or selectable (e.g., a support member can be selected based on its length to provide a particular distraction), and the distraction can be changed depending on an adjusted length of one or both of support members 920, 920' or based on the selected length of one or both of support members 920, 920'.

Figure 16:
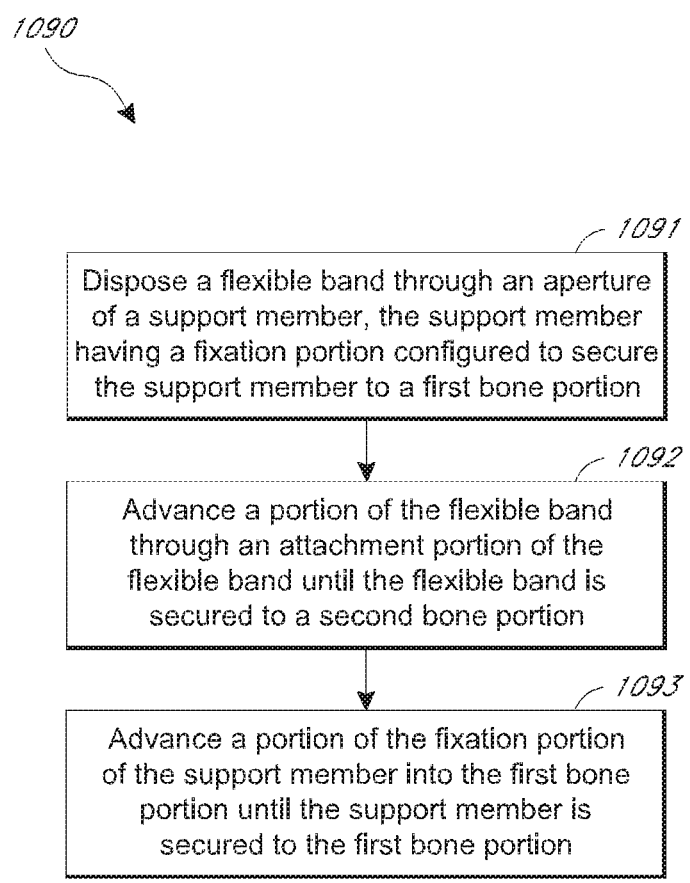
FIG. 16 is a flowchart illustrating a method of stabilizing a bone portion according to an embodiment.

FIG. 16 is a flowchart illustrating method 1090 of stabilizing a first bone portion to a second bone portion. The method 1090 includes disposing a flexible band through an aperture of a support member, at 1091. The support member has a fixation portion configured to secure the support member to a first bone portion. The method 1090 includes advancing a portion of the flexible band through an attachment portion of the flexible band until the flexible band is secured to a second bone portion, at 1092. The method 1090 includes advancing a portion of the fixation portion of the support member into the first bone portion until the support member is secured to the first bone portion, at 1093. In some embodiments, the method 1090 can includes disposing the flexible band through an aperture of a second support member. In such embodiments, the second support member can have a fixation portion configured to secure the second support member to a third bone portion. In such embodiments, the method can include advancing a portion of the fixation portion of the second support member into the third bone portion until the second support member is secured to the third bone portion. In some embodiments, the method 1090 can include adjusting a distance between a support portion of the support member and the fixation portion of the support member to define a distraction between the first bone portion and the second bone portion. In some embodiments, the method 1090 can include disposing the flexible band into contact with a fourth bone portion. In such embodiments, the method 1090 can include advancing the portion of the flexible band through the attachment portion of the flexible band includes advancing the portion of the flexible band through the attachment portion until the flexible band is secured to the second bone portion.

Figure 17:
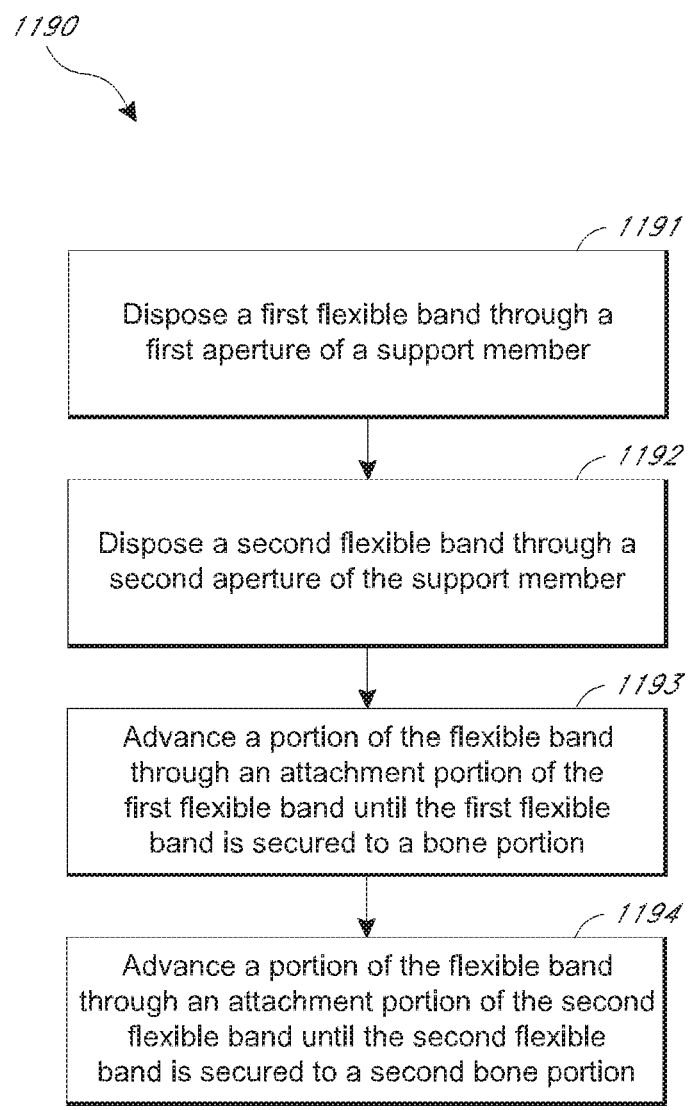
FIG. 17 is a flowchart illustrating a method of stabilizing a bone portion according to an embodiment.

FIG. 17 is a flowchart illustrating method 1190 of stabilizing a first bone portion to a second bone portion. The method 1190 includes disposing a first flexible band through a first aperture of a support member, at 1191. The method 1190 includes disposing a second flexible band through a second aperture of the support member, at 1192. The method 1190 includes advancing a portion of the flexible band through an attachment portion of the first flexible band until the first flexible band is secured to a bone portion, at 1193. The method 1190 includes advancing a portion of the flexible band through an attachment portion of the second flexible band until the second flexible band is secured to a second bone portion, at 1194. In some embodiments, the method 1190 can include disposing a third flexible band through a first aperture of a second support member. In such embodiments, the method 1190 can include disposing a fourth flexible band through a second aperture of the second support member. In such embodiments, the method 1190 can include advancing a portion of the third flexible band through an attachment portion of the third flexible band until the third flexible band is secured to a third bone portion. In such embodiments, the method 1190 can include advancing a portion of the fourth flexible band through an attachment portion of the fourth flexible band until the fourth flexible band is secured to a fourth bone portion. In some embodiments, the support member can have a length that is adjustable, and the method 1190 can includes adjusting the length of the support member to define a distraction between the first bone portion and the second bone portion.

Any of the embodiments, described above can be packaged independently or in any suitable combination. For example, in some embodiments, a kit can include at least flexible elongate body (e.g., a band) and a support member. For example, the band can be similar to or the same as the bands 140-940. In this manner, the flexible band is configured to stabilize, and or define a distraction between, a first bone portion and/or a second bone portion. The support member can include an interface portion configured to receive at least a portion of the flexible band. For example, the support member can be similar to or the same as support members 120-920. In this manner the support member is configured to stabilize, and or define a distraction between, a first bone portion and/or a second bone portion. The support member can includes a fixation portion configured to secure the support member to a second bone portion such that the first bone portion and the second bone portion are stabilized. In some embodiments, the kit can include additional bands and/or support members according to any of the embodiments described herein.

While various embodiments have been described above, it should be understood that they have been presented by way of example only, not limitation, and various changes in form and details may be made. For example, while the embodiments are illustrated here as being disposed about a spinous articular process of a first vertebra and a spinous articular process of a second vertebra, in other embodiments, a flexible elongate body (e.g., a band) can be disposed about another portion of one or more vertebra. In such embodiments, the band can be tightened about the vertebrae to offset or correct misalignment of a portion of the spine (e.g., scoliosis, or the like).

While the descriptions given are with reference to stabilizing vertebra, another bone(s) such as for example, a sternum and/or a rib(s) could be stabilized using the flexible fastening bands described herein. In another example, a flexible fastening band can be used to stabilize and/or fixate an intramedullary (IM) rod or nail. For example, the flexible fastening band can be used at different longitudinal locations along an IM rod or nail, and used to couple adjacent bone portions to the IM rod or nail. In such situations, a given flexible fastening band can fix a first bone portion, the IM rod or nail, and a second bone portion, all of which are positioned between the distal portion and the attachment connection of the flexible fastening band. In yet another example, a flexible fastening band can be used to stabilize and/or fixate a bone fragment. While various embodiments have been described above with regard to natural bone spaces, (e.g., the space between an inferior articulate process and a superior articulate process), in other embodiments, the bone spacing can be man-made (e.g., sternum split during a heart procedure), and/or due to an injury (e.g., broken bone).

Where methods described above indicate certain events occurring in certain order, the ordering of certain events can be modified. Additionally, certain of the events can be performed concurrently in a parallel process when possible, as well as performed sequentially as described above. For example, while the method 1090 described above includes advancing a portion of the band into the attachment connection prior to advancing the a portion of the fixation portion, in some embodiments, the portion of the fixation portion can be at least partially advanced into a bone portion prior to the portion of the band being advanced through the attachment portion. In some embodiments, at least a portion of the advancing of the portion of the fixation portion into the bone portion and at least a portion of the advancing of the portion of the band into the attachment connection can be done concurrently (e.g., simultaneously or alternatively in relatively small increments).

Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. An apparatus, comprising:
 a flexible elongate body comprising a distal end portion, a body portion, and a proximal end portion, wherein the flexible elongate body comprises a longitudinal axis extending from the distal end portion to the proximal end portion, the proximal end portion comprising an attachment portion that is configured to receive the distal end portion and the body portion to form a loop around a first bone portion, wherein the attachment portion is configured to permit movement of the body portion in a first direction but substantially limit the movement of the body portion in a second direction, wherein the attachment portion is monolithically formed with the flexible elongate body, wherein the attachment portion comprises a lumen configured to receive the distal end portion, wherein the lumen is transverse to the longitudinal axis; and
 a support member configured to couple to the flexible elongate body and a second bone portion, wherein the support member defines a distraction distance between the first bone portion and the second bone portion, wherein the support member comprises:
  a first component;
  a second component; and
  a third component, wherein the first component is configured to couple to the third component at a first point along the length of the third component, wherein the second component is configured to couple to the third component at a second point along the length of the third component, wherein the distance between the first point and the second point is configured to be increased or decreased to adjust the distraction distance between the first bone portion and the second bone portion.

2. The apparatus of claim 1,
 wherein the first component comprises a first coupler portion and an aperture configured to receive the flexible elongate body;
 wherein the second component comprises a second coupler portion; and
 wherein the third component is configured to be coupled to the first coupler portion and the second coupler portion.

3. The apparatus of claim 2, wherein the first component of the support member is configured to be coupled to the third component of the support member via a setscrew.

4. The apparatus of claim 2, wherein the third component is a rod.

5. The apparatus of claim 2, wherein the second component comprises a bone screw.

6. The apparatus of claim 1, wherein the second component comprises a second flexible elongate body configured to be coupled to the second bone portion.

7. The apparatus of claim 1, wherein the second component comprises a fixation portion configured to be coupled to the second bone portion.

8. The apparatus of claim 1, wherein the support member comprises:
 a second flexible elongate body comprising a distal end portion, a body portion, and an attachment portion that is configured to receive the distal end portion.

9. The apparatus of claim 1, further comprising a second support member configured to couple to the flexible elongate body.

10. An apparatus, comprising:
 a flexible elongate body comprising a distal end portion, a body portion, and a proximal end portion, the proximal end portion comprising an attachment portion that is configured to receive the distal end portion and the body portion when the body portion couples to a first vertebra, wherein the attachment portion is monolithically formed with the flexible elongate body; and
 a support member configured to couple to the flexible elongate body and a second vertebra, wherein the support member defines a distraction distance between the first vertebra and the second vertebra, wherein the support member comprises:
  a first component;
  a second component; and
  a third component, wherein the first component is configured to couple to the third component at a first point along the length of the third component, wherein the second component is configured to couple to the third component at a second point along the length of the third component, wherein the first point and the second point are spaced apart to define the distraction distance between the first vertebra and the second vertebra, wherein the distraction distance is adjustable.

11. The apparatus of claim 10, wherein the support member comprises a first fixation portion and a second fixation portion.

12. The apparatus of claim 10, wherein the support member comprises a set screw to maintain the distraction distance.

13. The apparatus of claim 10, wherein the support member comprises a coupler portion configured to adjust the distraction distance.

14. A kit, comprising:
 a flexible band configured to be coupled to a first vertebra, the flexible band comprising a distal end portion, a body portion, and a proximal end portion, the proximal end portion comprising an attachment portion that is configured to receive the distal end portion and the body portion, wherein the attachment portion is monolithically formed with the flexible band; and a support member configured to couple to the flexible band and a second vertebra, wherein the support member defines a distraction distance between the first vertebra and the second vertebra, wherein the support member comprises:

a first component comprising an aperture configured to receive the distal end portion of the flexible band, a second component comprising a fastener configured to advance into the second vertebra, and a third component disposed between the first component and the second component, wherein third component is configured to be coupled to a coupler portion of the first component at a first point and coupled to a coupler portion of the second component at a second point, wherein a length of the third component between the first point and the second point defines the distraction distance between the first vertebra and the second vertebra, wherein the length of the third component between the first point and the second point is adjustable.

15. The kit of claim 14, wherein the support member is a first support member, the kit further comprising: a second support member.

* * * * *